United States Patent
Mohammadi et al.

(10) Patent No.: US 11,931,147 B2
(45) Date of Patent: *Mar. 19, 2024

(54) SYSTEM AND METHOD FOR ROBUST PULSE OXIMETRY

(71) Applicant: Apple Inc., Cupertino, CA (US)

(72) Inventors: Saeed Mohammadi, Sunnyvale, CA (US); Albert E. Cerussi, San Jose, CA (US); Paul D. Mannheimer, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 17/663,411

(22) Filed: May 13, 2022

(65) Prior Publication Data

US 2022/0273207 A1 Sep. 1, 2022

Related U.S. Application Data

(63) Continuation of application No. 16/583,211, filed on Sep. 25, 2019, now Pat. No. 11,331,016.

(Continued)

(51) Int. Cl.
*A61B 5/1455* (2006.01)
*A61B 5/00* (2006.01)
*A61B 5/024* (2006.01)

(52) U.S. Cl.
CPC .......... *A61B 5/14552* (2013.01); *A61B 5/681* (2013.01); *A61B 5/7203* (2013.01);
(Continued)

(58) Field of Classification Search
CPC ..... A61B 5/1455; A61B 5/14551; A61B 5/72; A61B 5/7203; A61B 5/721; A61B 5/7221
See application file for complete search history.

(56) References Cited

U.S. PATENT DOCUMENTS

| 5,431,170 A | 7/1995 | Mathews |
| 5,483,261 A | 1/1996 | Yasutake |

(Continued)

FOREIGN PATENT DOCUMENTS

| JP | 2000-163031 A | 6/2000 |
| JP | 2002-342033 A | 11/2002 |

OTHER PUBLICATIONS

Non-Final Office Action received for U.S. Appl. No. 16/583,211, dated Jun. 24, 2021, 7 pages.

(Continued)

*Primary Examiner* — Eric F Winakur
(74) *Attorney, Agent, or Firm* — Kubota & Basol LLP

(57) ABSTRACT

Robust estimation of a characteristic of a user's physiological signals can be achieved by filtering or classifying samples. Rather than estimating the characteristic of the user's physiological signals based on each sample at a first wavelength and a second wavelength, a robust system and method can, in some examples, estimate the characteristic using samples at the first wavelength and the second wavelength that meet one or more criteria and filter out samples that fail to meet the one or more criteria. In some examples, the system and method can weight samples based on the one or more criteria, and estimate the characteristic using the weighted samples. Samples failing to meet the one or more criteria can be given less weight or no weight in the estimation. The one or more criteria can include a criterion based on at least the physiological signal at a third wavelength.

20 Claims, 7 Drawing Sheets

Related U.S. Application Data

(60) Provisional application No. 62/739,039, filed on Sep. 28, 2018.

(52) U.S. Cl.
CPC ........ *A61B 5/7221* (2013.01); *A61B 5/02433* (2013.01); *A61B 5/02438* (2013.01); *A61B 2562/0238* (2013.01); *A61B 2562/0242* (2013.01); *A61B 2562/046* (2013.01)

(56) References Cited

U.S. PATENT DOCUMENTS

| | | | |
|---|---|---|---|
| 5,488,204 | A | 1/1996 | Mead et al. |
| 5,825,352 | A | 10/1998 | Bisset et al. |
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,690,387 | B2 | 2/2004 | Zimmerman et al. |
| 7,015,894 | B2 | 3/2006 | Morohoshi |
| 7,184,064 | B2 | 2/2007 | Zimmerman et al. |
| 7,663,607 | B2 | 2/2010 | Hotelling et al. |
| 8,280,469 | B2 | 10/2012 | Baker, Jr. |
| 8,479,122 | B2 | 7/2013 | Hotelling et al. |
| 11,331,016 | B1 | 5/2022 | Mohammadi et al. |
| 2006/0197753 | A1 | 9/2006 | Hotelling |
| 2006/0211925 | A1 | 9/2006 | Lamego et al. |
| 2007/0129616 | A1 | 6/2007 | Rantala |
| 2013/0109936 | A1 | 5/2013 | Mannheimer et al. |
| 2015/0018647 | A1 | 1/2015 | Mandel et al. |
| 2017/0319114 | A1 | 11/2017 | Kaestle |
| 2017/0347957 | A1 | 12/2017 | Van Den Ende et al. |

OTHER PUBLICATIONS

Notice of Allowance received for U.S. Appl. No. 16/583,211, dated Jan. 18, 2022, 9 pages.

Lee et al., "A Multi-Touch Three Dimensional Touch-Sensitive Tablet", CHI'85 Proceedings, Apr. 1985, pp. 21-25.

Rubine, Dean, "Combining Gestures and Direct Manipulation", CHI'92, May 3-7, 1992, pp. 659-660.

Rubine, Dean H., "The Automatic Recognition of Gestures", CMU-CS-91-202, Submitted in Partial Fulfillment of the Requirements for the Degree of Doctor of Philosophy in Computer Science at Carnegie Mellon University, Dec. 1991, 285 pages.

Westerman, Wayne, "Hand Tracking, Finger Identification, and Chordic Manipulation on a Multi-Touch Surface", A Dissertation Submitted to the Faculty of the University of Delaware in Partial Fulfillment of the Requirements for the Degree of Doctor of Philosophy in Electrical Engineering, 1999, 363 pages.

PHOTOPLETHYSMOGRAPHY (PPG) SIGNAL

PHOTOPLETHYSMOGRAPHY (PPG) SIGNAL

SYSTEM AND METHOD FOR ROBUST PULSE OXIMETRY

CROSS-REFERENCE TO RELATED APPLICATIONS

This application is a continuation of U.S. patent application Ser. No. 16/583,211, filed on Sep. 25, 2019, which claims benefit of U.S. Provisional Application No. 62/739,039, filed Sep. 28, 2018, which are hereby incorporated by reference in their entireties for all purposes.

FIELD

This relates generally to pulse oximetry systems and methods, and more particularly, to pulse oximetry systems and methods utilizing measurements at an additional wavelength to improve robustness of pulse oximetry measurements.

BACKGROUND

Information or characteristics (e.g., pulse rate or arterial oxygen saturation) of a user's physiological signals can be determined by pulse oximetry systems and methods. In a basic form, pulse oximetry systems and methods can utilize one or more light emitters to illuminate a user's tissue and one or more light detectors to receive light that enters and probes a subsurface volume of tissue. The light sources and light detectors can be in contact with the tissue or can be remote (i.e., not in contact) to the tissue surface. For example, arterial oxygen saturation can be estimated based on a perfusion index ratio for two different wavelengths of light. However, the estimates of information or characteristics of a user's physiological signals may be inaccurate when the light emitters or light detectors are not in good contact, oriented differently with respect to the tissue surface than expected, or there are physiological anomalies in the path of light from light emitters to light detectors.

SUMMARY

This relates to systems and methods for robust estimation of a characteristic of a user's physiological signals. Rather than estimating the characteristic of the user's physiological signals based on each sample at a first wavelength and a second wavelength, the system and method can, in some examples, estimate the characteristic using samples at the first wavelength and the second wavelength that meet one or more criteria and filter out samples that fail to meet the one or more criteria. In some examples, the system and method can weight samples based on the one or more criteria (e.g., using a confidence value), and estimate the characteristic using the weighted samples. Samples failing to meet the one or more criteria can be given less weight or no weight in the estimation. The one or more criteria can include a criterion based on at least the physiological signal at a third wavelength.

DETAILED DESCRIPTION

Figure 1A:
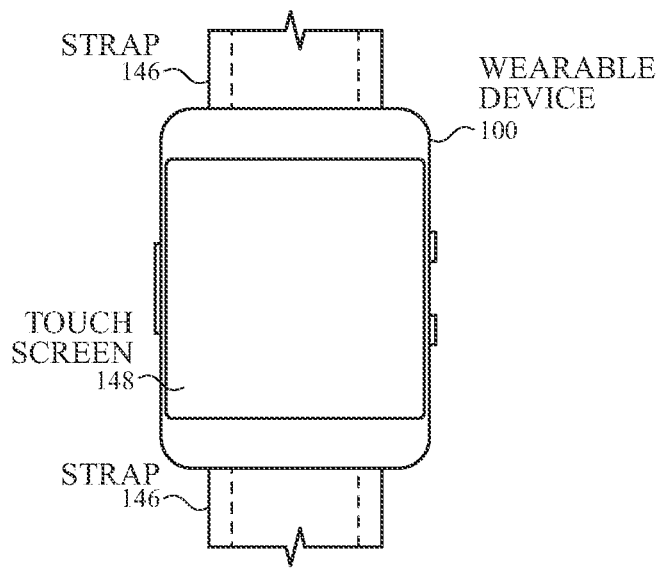
FIGS. 1A-1B illustrate views of an exemplary electronic device for measuring physiological signals according to examples of the disclosure.

In the following description of examples, reference is made to the accompanying drawings in which it is shown by way of illustration specific examples that can be practiced. It is to be understood that other examples can be used and structural changes can be made without departing from the scope of the various examples.

This relates to systems and methods for robust estimation of a characteristic (e.g., pulse rate and arterial blood oxygen saturation) using a user's physiological signals. As used herein, physiological signals refer to signals generated by a physiological sensor (e.g., a photoplethysmogram (PPG) signal) that can be used for estimating the physiological characteristic (or condition) of a patient or user. A user's physiological signals can be determined by measurements using pulse oximetry systems. Such pulse oximetry systems can be designed to be sensitive to changes in the red blood cell number/concentration, volume, or blood oxygen state included in the sample or a user's vasculature. In a basic form, pulse oximetry systems can employ a light emitter that injects light into the user's tissue and a light detector to receive light that reflects and/or scatters and exits the tissue. The light emitter(s) and light detector(s) can be in contact or can be remote to (i.e., not in contact with) the tissue. In some examples, at least a portion of the photon path length interacts with tissue subsurface structures. Pulse oximetry systems can include, but are not limited to, PPG systems and arterial blood oxygen saturation (SpO2) systems. PPG and SpO2 systems can estimate a characteristic of physiological signals based on the attenuation of light (as measured by a physiological signal sensor) that varies over the duration of the cardiac cycle. Attenuation can be due to absorption, and/or scattering resulting from physiological/mechanical changes. Physiological/mechanical changes can include, but are not limited to, red blood cell number, cell/blood volume, red blood cell orientation, red blood cell/blood velocity, shear force, location/spatial distribution, concentration in the tissue, or other tissue properties (e.g., hydration, etc.), or a combination thereof.

Rather than estimating a characteristic (e.g., arterial blood oxygen saturation) of the user's physiological signals using each sample at a first wavelength and a second wavelength, the system and method can, in some examples, estimate the characteristic using samples at the first wavelength and the second wavelength that meet one or more criteria and filter out samples that fail to meet the one or more criteria. In some examples, the system and method can weight samples based on the one or more criteria (e.g., using a confidence value), and estimate the characteristic using the weighted samples. Samples failing to meet the one or more criteria can be given less weight or no weight in the estimation. The one or more criteria can include a criterion based on at least the physiological signal at a third wavelength. Although primarily described herein as using physiological signals at first and second wavelengths for estimating the physiological characteristic and at least a physiological signal at a third wavelength for filtering/classifying samples, it should be understood that the physiological characteristic can be estimated using physiological signals at more than two wavelengths and the filtering/classifying can be based on more than one wavelength. In some examples, the at least the physiological signal at the third wavelength may not be used for estimating the physiological characteristic.

Figure 1C:
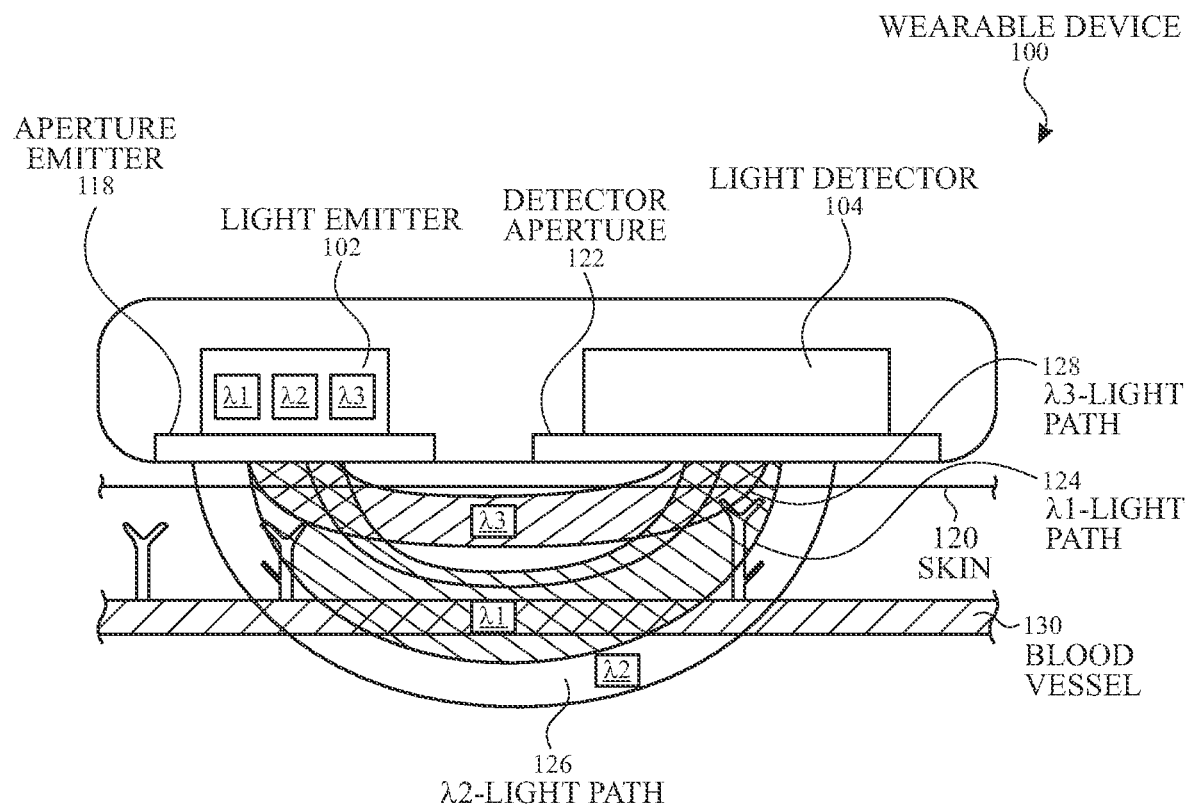
FIG. 1C illustrates a cross-sectional view of exemplary wearable device 100 including one or more light emitters and one or more light detectors for measuring a user's physiological signal according to examples of the disclosure.
Figure 1B:
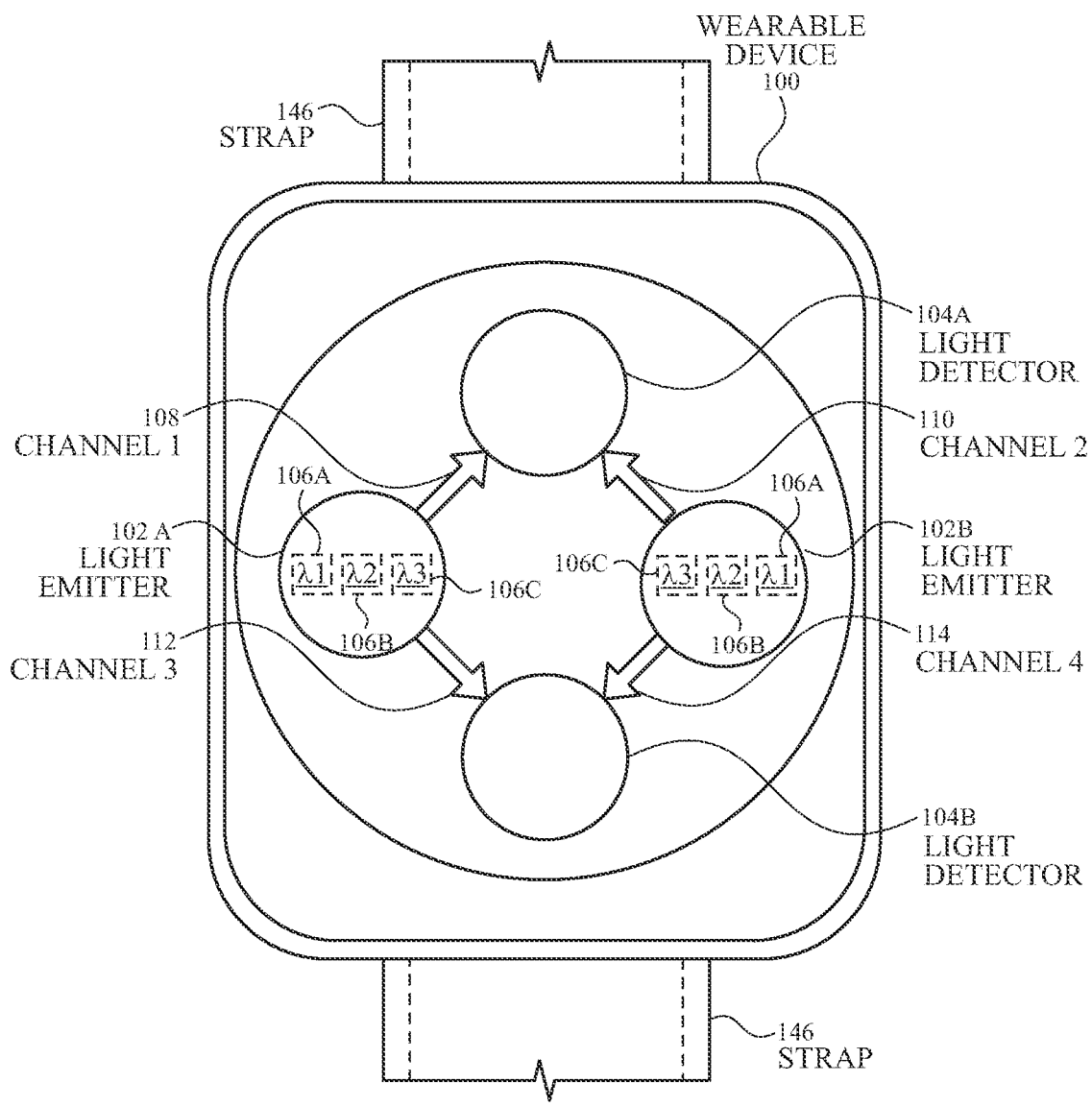

FIGS. 1A-1B illustrate views of an exemplary electronic device for measuring physiological signals according to examples of the disclosure. FIG. 1A illustrates a top view of an exemplary wearable device 100 that can include a touch screen 148 and can be attached to a user using a strap 146 or other fastener. FIG. 1B illustrates a bottom view (underside) of exemplary wearable device 100 including one or more light emitters and one or more light detectors for measuring a user's physiological signal according to examples of the disclosure. For example, FIG. 1B illustrates device 100 that can include light emitters 102A-B and light detectors 104A-B. Device 100 can be positioned such that light emitters 102A-B and light detectors 104A-B are proximate to a user's skin or any other tissue site. For example, device 100 can be held in the user's hand or strapped to the user's wrist, among other possibilities. In some examples, light emitters 102A-B and light detectors 104A-B can be in close proximity (e.g., within a threshold distance, such as 5 mm, for example) to the surface of user's skin or can be physically contacting a surface of user's skin, which can reduce the amount of detected light that has not traveled through tissue.

In some examples, light emitters 102A-B can include one or more light sources to generate light at different wavelengths. For example, FIG. 1B illustrates each light emitter 102A-B including three light sources 106A-C (e.g., light emitting diodes (LEDs) or organic light emitting diodes (OLEDs)) configured to generate light at at least wavelengths λ1, λ2, and λ3, respectively. Although three wavelengths are shown, in some examples, device 100 may include light sources at fewer or more wavelengths. Additionally, in some examples, each light emitter can include one light source with a tunable wavelength (e.g., voltage or current controlled) or with different filters, rather than using a different light source for each wavelength. In some examples, each light emitter 102A-B can be optically coupled to each light detector 104 for each wavelength. For example, light emitter 102A can be optically coupled to both light detectors 104A-B and light emitter 102B can be optically coupled to both light detectors 104A-B. Light emitter 102A can be configured to emit light (at one or more wavelengths) and generate one or more light paths detected by light detector 104A and one or more light paths detected by light detector 104B. Light emitter 102B can also be configured to emit light (at one or more wavelengths) and generate one or more light paths detected by light detector 104A and one or more light paths detected by light detector 104B. As illustrated in FIG. 1B, a first channel 108 can be used to measure signal at light detector 104A from light emitter 102A (at each respective wavelength), a second channel 110 can be used to measure signal at light detector 104A from light emitter 102B (at each respective wavelength), a third channel 112 can be used to measure signal at light detector 104B from light emitter 102A (at each respective wavelength), and a fourth channel 114 can be used to measure signal at light detector 104B from light emitter 102B (at each respective wavelength). The measured signal at each detector can include light measured from various light paths (e.g., through the skin and/or air) between the respective emitter and detector of the channel.

Device 100 can also include processing circuitry to process light detected from light detectors 104A-B to determine the user's physiological signals and extract information (e.g., one or more characteristics) from the physiological signals. In some examples, a physiological characteristic can be a heart rate or a hemoglobin oxygen saturation level (e.g., an arterial oxygen saturation ($SpO_2$)). In some examples, the processing circuitry can remove or reduce motion artifacts from the physiological signals to account for non-cardiac-induced pulsatile blood volume changes. Additionally, as described herein, the processing circuitry can remove or reduce the impact of measurements that may produce incorrect or inaccurate estimates of the characteristic.

FIG. 1C illustrates a cross-sectional view of exemplary wearable device 100 including one or more light emitters and one or more light detectors for measuring a user's physiological signal according to examples of the disclosure. As illustrated in FIG. 1C, light emitter 102 can generate light at one or more wavelengths that can exit aperture 118 (e.g., a window). The light can be directed towards, and incident upon, the user's skin 120 and some of the light can be reflected back toward device 100. The light can reenter device through aperture 122 (e.g., a window) and be detected by light detector 104. In some examples, apertures 118 and 122 (and thereby light emitter 102 and light detector 104) can be in close proximity (e.g., within a threshold distance, such as 5 mm, 1 mm, 0.1 mm, etc.) to the surface of user's skin or can be physically contacting a surface of user's skin, which can reduce the amount of detected light that has not traveled through tissue. A portion of light can be absorbed by molecules in skin 120, vasculature, and/or blood. Pulsatile blood flow in the user can lead to changes in the arterial vessel diameters, tissue hemoglobin concentration or volume, red blood cell orientation, velocity, or other physical states during a pressure change (e.g., diastole to systole), which can be included in light (e.g., via a scattering or absorption contrast mechanism) within the field of view of light detector 104. In some examples, oxygen saturation in the blood can be estimated based on a ratio between physiological signal measurements (e.g., light intensity signals at light detectors) at two (or more) wavelengths. For example, oxygen saturation can be estimated based on a relative modulation ratio at two or more wavelengths. In some examples, the modulation ratio can be a perfusion index (PI) ratio based on physiological signal measurements at two or more wavelengths. Although the intensity of the physiological signal (or more generally the magnitude of each independent wavelength measurement) may change due to variations in the pulsations of blood, movement and the heterogeneity of tissue, the relative modulation ratio (e.g., between red light and infrared light)

can be relatively stable indicator of oxygen saturation (e.g., via an empirical mapping between the relative modulation ratio and oxygen saturation).

FIG. 1C illustrates exemplary optical paths for three different wavelengths $\lambda 1$, $\lambda 2$ and $\lambda 3$. Optical path 124 can correspond to wavelength $\lambda 1$ (e.g., in the wavelength range of 620 nm-750 nm) and optical path 126 can correspond to wavelength $\lambda 2$ (e.g., in the wavelength range of 750 nm-1400 nm). In some examples, wavelength $\lambda 1$ can be in the range of visible light (e.g., 400 nm-700 nm) and wavelength $\lambda 2$ can be in the range of near-infrared (NIR) light (e.g., 700-1100 nm), which can be strongly absorbed by blood and other molecules in the user's tissue and blood. In some examples, wavelength $\lambda 1$ can be red light and wavelength $\lambda 2$ can be IR light. Optical path 128 can correspond to wavelength $\lambda 3$ (e.g., in the wavelength range of 495 nm-570 nm). In some examples, $\lambda 3$ can be in a lower wavelength range of visible light (e.g., 400 nm-495 nm), such as blue light, or near ultraviolet light (e.g., 300 nm-400 nm), or other portions of the visible light, NIR, short-wave IR spectra. It should be understood that these wavelength ranges are for exemplary purposes and different wavelength ranges are possible for $\lambda 1$, $\lambda 2$, and $\lambda 3$ (or any additional wavelengths). As shown in FIG. 1C, in some examples, different wavelengths can penetrate different depths within skin 120. For example, optical paths 124 and 126 corresponding to wavelengths $\lambda 1$ and $\lambda 2$ can penetrate more deeply within the skin 120 and underlying tissue, whereas optical path 128 corresponding to wavelength $\lambda 3$ can penetrate less deeply within skin 120 and the underlying tissue. Additionally, although the optical paths may penetrate different depths, it is understood that light at some wavelengths can penetrate a variety of depths including shallower and deeper within the tissue. In some examples, such optical paths can be useful as a reference wavelength for estimating a characteristic of a user's physiological signals and/or for filtering/classifying samples.

Skin 120 and underlying tissue can include the blood vessels (arterial and venous) such as blood vessel 130. Light emitter 102 and light sensor 104 can be located and wavelengths can be selected such that optical paths 124 and 126 corresponding to wavelengths $\lambda 1$ and $\lambda 2$ can be sensitive to arterial blood volume changes to enable an estimation of the characteristic of a user's physiological signals. In some examples, measurements at one or more different wavelengths (e.g., corresponding to at least optical path 128 at wavelength $\lambda 3$) can be used to identify which measurements at wavelengths $\lambda 1$ and $\lambda 2$ may be suitable for physiological signal processing and/or how to processes the measurements at wavelengths $\lambda 1$ and $\lambda 2$ in the physiological signal processing, as described in more detail below. In some examples, measurements at wavelength $\lambda 3$ (alone or in conjunction with a reference measurement at a different wavelength) can indicate measurement conditions susceptible to inaccurate characteristic estimates based on wavelengths $\lambda 1$ and $\lambda 2$. In some examples, the conditions can include poor contact between the physiological sensor (e.g., light emitters and light detectors), an unexpected orientation of the tissue and the sensor, or other physiological anomalies of the tissue structure. For example, while device 100 is properly secured to skin 120, measurements at wavelengths $\lambda 1$ and $\lambda 2$ can be sensitive to arterial blood volume changes. However, while device 100 is not properly secured to skin 120, measurements at wavelength $\lambda 3$ from optical path 128 may be less sensitive or lose sensitivity to arterial blood volume changes.

In some examples, a range of contact forces between the skin and a device including the physiological signal sensor(s) can be defined as "good contact" and contact forces outside the range of contact forces can be defined as "poor contact," which can be susceptible to inaccurate characteristic estimates. In some examples, the range of contact forces can be between 1-4 Newtons for "good contact" and less than 1N or greater than 4N for "poor contact." In some examples, a different range can be defined by different upper and lower bounds (e.g., 0.5N-10N, 2N-6N, 1N-8N, etc.). In some examples, rather than using a range of contact forces, "poor contact" and "good contact" can be defined using one threshold contact force. For example, less than 1N can be considered "poor contact" and greater than or equal to 1N can be considered "good contact. In some examples, the threshold value can be different than 1N (e.g., 0.5N, 0.9N, 1.2N, 2N, etc.).

Figure 2A:
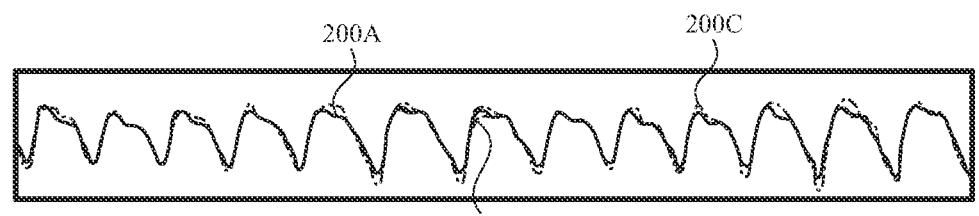
FIGS. 2A-2D illustrate photoplethysmogram signals measured at different wavelengths for different contact conditions according to examples of the disclosure.
Figure 2B:
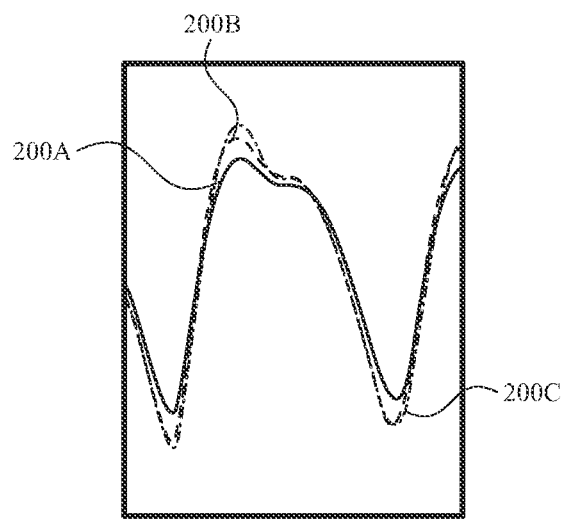
Figure 2C:
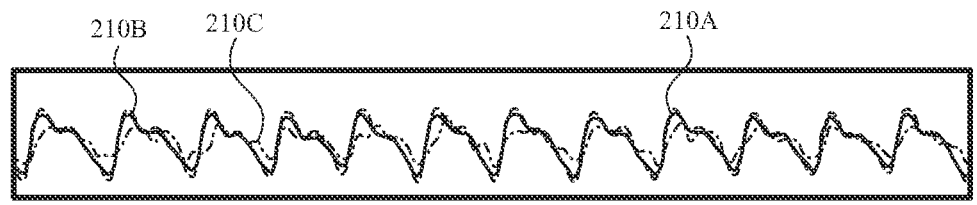
Figure 2D:
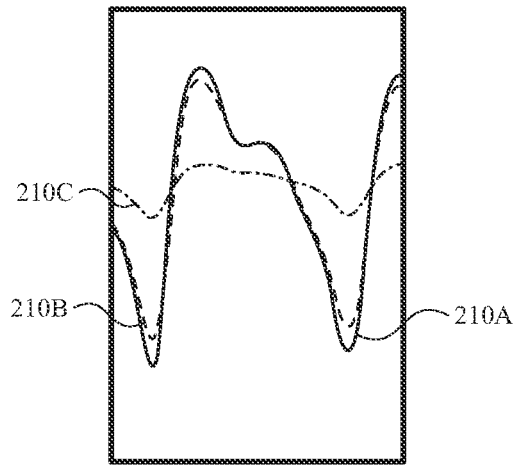

FIGS. 2A-2D illustrate example photoplethysmogram (PPG) signals measured at different wavelengths for different contact conditions according to examples of the disclosure. The PPG signals can include cyclical "beats" (or "pulses") corresponding to a heartbeat (e.g., each "beat" or "pulse" indicative of one occurrence of the repeating cardiac cycle). FIGS. 2A-2B illustrate a PPG signal for each of wavelengths $\lambda 1$, $\lambda 2$ and $\lambda 3$ while device 100 is properly secured to skin 120 (good contact) and FIGS. 2C-2D illustrate a PPG signal for each of wavelengths $\lambda 1$, $\lambda 2$ and $\lambda 3$ while device 100 is not properly secured to skin 120 (light or poor contact). FIG. 2A illustrates PPG signals 200A, 200B, 200C with multiple beats and FIG. 2B illustrates a larger view of an exemplary beat, in which the waveform shapes of PPG signals 200A-C can be similar and correspond to pulsatile blood information. FIG. 2C illustrates PPG signals 210A, 210B, 210C with multiple beats and FIG. 2D illustrates a larger view of an exemplary beat, in which the waveform shapes of PPG signals 210A-B can be similar and correspond to pulsatile blood information for wavelengths $\lambda 1$ and $\lambda 2$, but the waveform of PPG signal 210C can be different in shape and/or relative amplitude and may or may not correspond to pulsatile blood information for wavelength $\lambda 3$. Although beats are shown, it is understood that the methods described herein can be applied based on instantaneous measurements, on a beat-by-beat basis or on an average of multiple beats. As described herein, measurements at wavelength $\lambda 3$ (e.g., green light, blue light, etc.) can be used to estimate the contact condition and identify which measurements at wavelengths $\lambda 1$ and $\lambda 2$ (e.g., red light and IR light) may be suitable for physiological signal processing and/or how to processes the measurements at wavelengths $\lambda 1$ and $\lambda 2$ in the physiological signal processing. As described above, other conditions aside from contact condition may result in an inaccurate estimate of the physiological signal characteristic. For example, while device 100 is at an unexpected orientation relative to skin 120 or a transient or permanent tissue anomaly is present, measurements at wavelengths $\lambda 1$ and $\lambda 2$ may result in inaccurate measurements of the physiological signal characteristic. These conditions may also be estimated based on measurements at wavelength $\lambda 3$ to identify which measurements may be suitable for processing (and/or how to process the measurements at wavelengths $\lambda 1$ and $\lambda 2$ in the physiological signal processing). In some examples, when these conditions are estimated based on wavelengths $\lambda 3$ (e.g., when the device is outside a threshold distance from the surface of the user's skin or in poor contact), the device can forgo estimating or reporting an estimated physiological characteristic based on wavelengths $\lambda 1$ and $\lambda 2$.

Figure 1D:
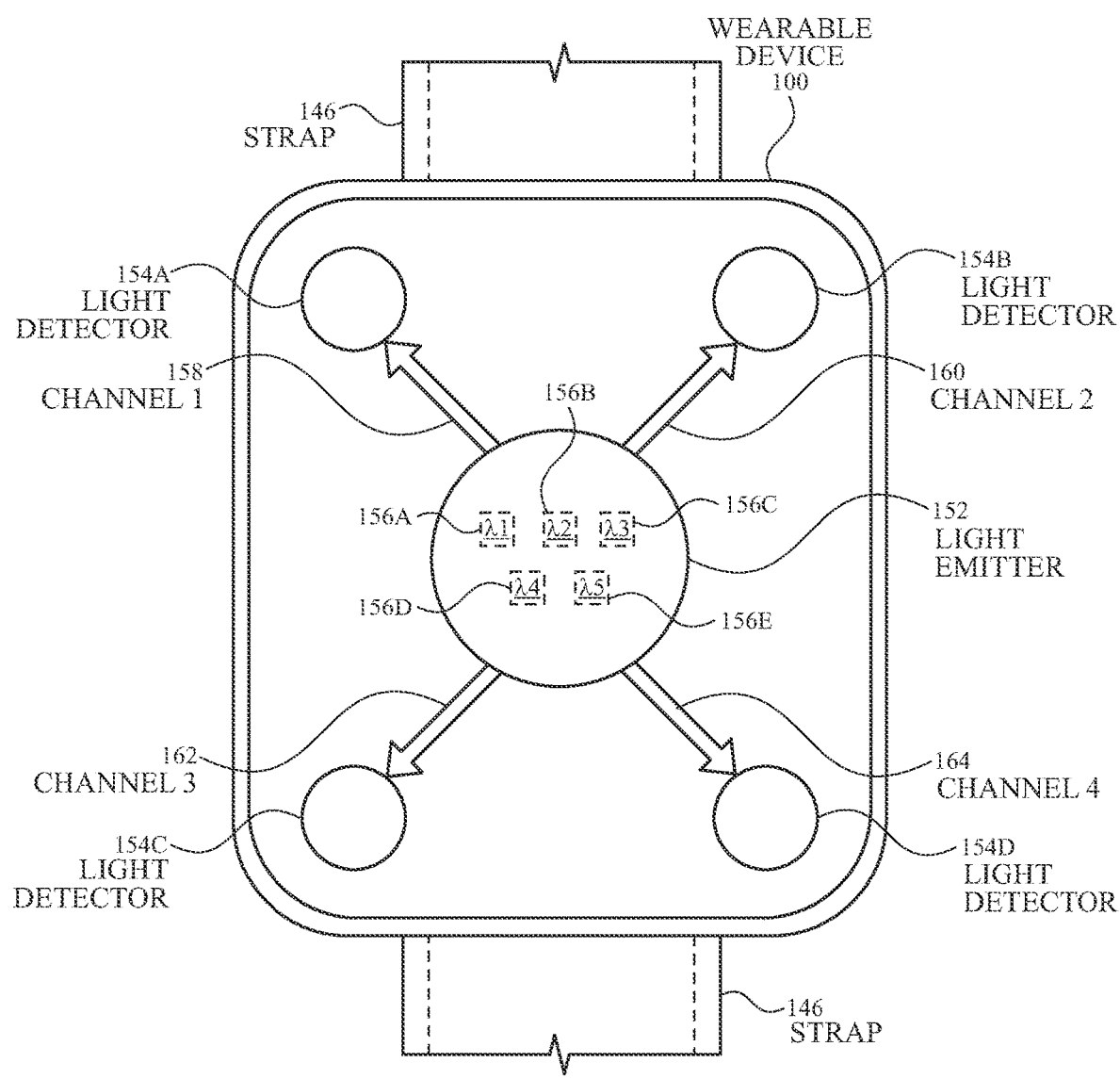
FIG. 1D illustrates an alternative arrangement of light emitters and light detectors on the underside of an exemplary electronic device for measuring physiological signals according to examples of the disclosure.

FIG. 1D illustrates an alternative arrangement of light emitters and light detectors on the underside of an exemplary electronic device for measuring physiological signals according to examples of the disclosure. FIG. 1D illustrates device 100 that can include light emitter 152 in a center of the device and light detectors 154A-D. Light emitter 152 can include one or more light sources to generate light at different wavelengths. For example, FIG. 1D illustrates light emitter 152 including five light sources 156A-E (e.g., an LED or OLED) configured to generate light at wavelengths $\lambda 1$, $\lambda 2$, $\lambda 3$, $\lambda 4$ and $\lambda 5$, respectively. Although five wavelengths are shown, in some examples, device 100 may include light sources at fewer or more wavelengths (or one tunable/filterable light source) or may include different types of light sources (e.g., laser diodes). Light emitter 152 can be optically coupled to one or more (or each of) light detectors 154A-D for one or more (or each of the) wavelengths. In some examples, light emitter 152 can be configured to emit light (at one or more wavelengths) and generate one or more light paths detected by light detector 154A, one or more light paths detected by light detector 154B, one or more light paths detected by light detector 154C and one or more light paths detected by light detector 154D. As illustrated in FIG. 1D, a first channel 158 can be used to measure signal at light detector 154A from light emitter 152 (e.g., at each respective wavelength), a second channel 160 can be used to measure signal at light detector 154A from light emitter 152 (at each respective wavelength), a third channel 162 can be used to measure signal at light detector 104C from light emitter 152 (at each respective wavelength), and a fourth channel 164 can be used to measure signal at light detector 154D from light emitter 152 (at each respective wavelength). The measured signal at each detector (at each respective wavelength) can include light that has traversed various light paths (e.g., through the skin and/or air) between the respective emitter and detector of the channel.

Although FIGS. 1B and 1D illustrate four channels (each operable for emitting/detecting light at multiple wavelengths), in some examples, fewer or additional channels may be implemented. For example, a single channel including one light emitter and one light detector can be used. In some examples, additional light emitters and/or light detectors may be used to form additional channels. For example, adding one or more additional light detectors to the configurations in FIG. 1B or 1D can increase the number of channels.

In some examples, the signals from the one or more light emitters and one or more light detectors can be utilized to perform other functions aside from measuring the user's physiological signals and extracting information/characteristics from the physiological signals. For example, one or more light emitters and one or more light detectors can be configured for monitoring whether or not the device remains in contact with a user's skin (e.g., off-wrist detection).

Figure 3:
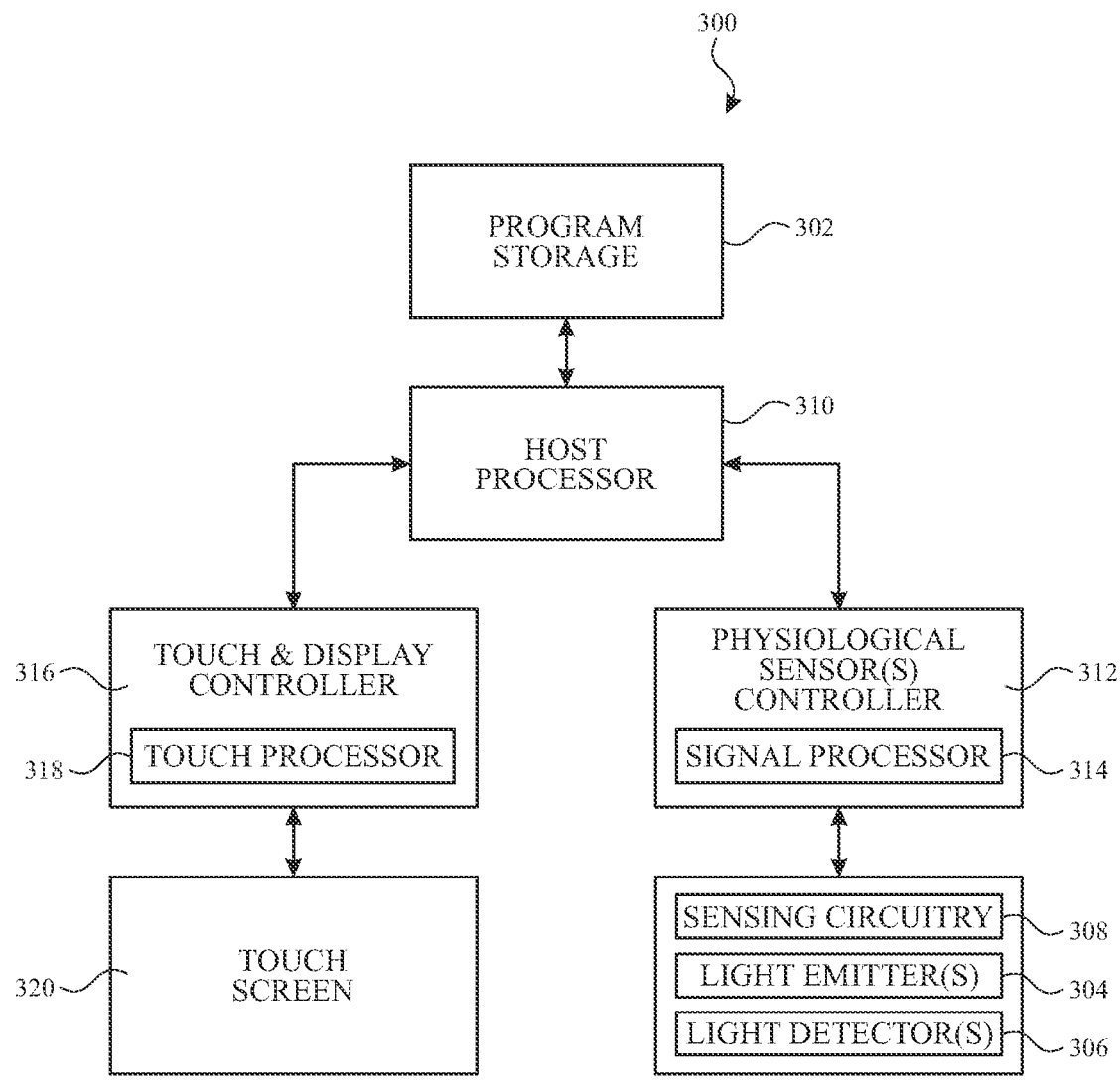
FIG. 3 illustrates an exemplary block diagram of a computing system for measuring a physiological signal and/or extracting a characteristic from the physiological signal according to examples of the disclosure.

FIG. 3 illustrates an exemplary block diagram of a computing system for measuring a physiological signal and/or extracting a characteristic (e.g., blood oxygen saturation) from the physiological signal according to examples of the disclosure. Although primarily described herein as a wearable device, the computing system may alternatively be implemented partially or fully in a non-wearable device. For example, the sensors and/or processing described herein can be implemented partially or fully in a mobile telephone, media player, tablet computer, personal computer, server, etc. In some examples, the light emitters and light detectors can be implemented in a wearable device (e.g., a wristwatch) and the processing of the data can be performed in a non-wearable device (e.g., a mobile phone). Processing and/or storage of the physiological signals in a separate device can enable the device including the physiological sensors (e.g., a wrist watch) to be space and power efficient (which can be important features for portable/wearable devices).

Computing system 300 can correspond to device 100 illustrated in FIGS. 1A-1D (or may be implemented in other wearable or non-wearable electronic devices). Computing system 300 can include a processor 310 (or more than one processor) configured to execute instructions and to carry out operations associated with computing system 300. For example, using instructions retrieved from program storage 302, processor 310 can control the reception and manipulation of input and output data between components of computing system 300. Processor 310 can be a single-chip processor (e.g., an application specific integrated circuit) or can be implemented with multiple components/circuits.

In some examples, processor 310 together with an operating system can operate to execute computer code and produce and use data. The computer code and data can reside within a program storage 302 that can be operatively coupled to processor 310. Program storage 302 can generally provide a place to hold data that is being used by computing system 300. Program storage block 302 can be any non-transitory computer-readable storage medium, and can store, for example, history and/or pattern data relating to PPG signals and relative modulation ratio (e.g., perfusion index ratio) values measured by a configuration of light emitter(s) 304 and light detector(s) 306 (e.g., as illustrated in FIG. 1B or 1D). By way of example, program storage 302 can include Read-Only Memory (ROM), Random-Access Memory (RAM), hard disk drive and/or the like. The computer code and data could also reside on a removable storage medium and loaded or installed onto computing system 300 when needed. Removable storage mediums include, for example, CD-ROM, DVD-ROM, Universal Serial Bus (USB), Secure Digital (SD), Compact Flash (CF), Memory Stick, Multi-Media Card (MMC) and/or a network component.

Computing system 300 can also include one or more input/output (I/O) controllers that can be operatively coupled to processor 310. I/O controllers can be configured to control interactions with one or more I/O devices (e.g., touch sensor panels, display screens, touch screens, physical buttons, dials, slider switches, joysticks, or keyboards). I/O controllers can operate by exchanging data between processor 310 and the I/O devices that desire to communicate with processor 310. The I/O devices and I/O controller can communicate through a data link. The data link can be a unidirectional or bidirectional link. In some cases, I/O devices can be connected to I/O controllers through wireless connections. A data link can, for example, correspond any wired or wireless connection including, but not limited to, PS/2, Universal Serial Bus (USB), Firewire, Thunderbolt, Wireless Direct, IR, RF, Wi-Fi, Bluetooth or the like.

For example, computing system 300 can include a physiological sensor controller 312 operatively coupled to processor 310 and to one or more physiological sensors. One of the physiological sensors can include light emitter(s) 304, light detector(s) 306 and corresponding sensing circuitry 308 (e.g., analog circuitry to measure signals at the detector, provide processing (e.g., amplification, filtering), and convert analog signals to digital signals). As described herein, light emitters 304 and light detectors 306 can be configured to generate and emit light into a user's skin and detect reflected and/or scattered light to measure a physiological signal (e.g., a PPG signal). The absorption and/or reflection of light at different wavelengths can also be used to determine a characteristic of the user (e.g., oxygen saturation, heart rate) and/or about the contact condition between the light emitters 304/light detectors 306 and the user's skin. Measured raw data from the light emitters 304, light detectors 306 and sensing circuitry 308 can be transferred to processor 310, and processor 310 can perform the signal processing described herein to estimate a characteristic (e.g., oxygen saturation, heart rate, etc.) of the user from the physiological signals. In some example, as described herein, the signal processing can include filtering to reject or weight measurements at one or more wavelengths. In some examples, measurements at a first and a second wavelength can be rejected or weighted based on measurements at a third wavelength. Processor 310 and/or physiological sensor controller 312 can operate light emitters 304, light detectors 306 and/or sensing circuitry 308 to measure data from the user. In some examples, physiological sensor controller 312 can include timing generation for light emitters 304, light detectors 306 and/or sensing circuitry 308 to sample, filter and/or convert (from analog to digital) signals measured from light at different wavelengths. Physiological sensor controller 312 can process the data in signal processor 314 and report outputs (e.g., PPG signal, relative modulation ratio, perfusion index, heart rate, etc.) to the processor 310. Signal processor 314 can be a digital signal processing circuit such as a digital signal processor (DSP). The analog data measured by the physiological sensors can be converted into digital data by an analog to digital converter (ADC), and the digital data from the physiological signals can be stored for processing in a buffer (e.g., a FIFO) or other volatile or non-volatile memory (not shown) in physiological sensor controller 312. In some examples, some light emitters and/or light detectors can be activated, while other light emitters and/or light detectors can be deactivated to conserve power, for example, or for time-multiplexing. In some examples, processor 310 and/or physiological sensor controller 312 can store the raw data and/or processed information in memory (e.g., ROM or RAM) for historical tracking or for future diagnostic purposes. Additional detail regarding physiological sensors and processing physiological signals is described below.

Computing system 300 can also include, in some examples, a touch and display controller 316 operatively coupled to processor 310 and to touch screen 320. Touch screen 320 can be configured to display visual output in a graphical user interface (GUI), for example. The visual output can include text, graphics, video, and any combination thereof. In some examples, the visual output can include a text or graphical representation of the physiological signal (e.g., a PPG waveform) or a characteristic of the physiological signal (e.g., oxygen saturation, heart rate, etc.) Touch screen can be any type of display including a liquid crystal display (LCD), a light emitting polymer display (LPD), an electroluminescent display (ELD), a field emission display (FED), a light emitting diode (LED) display, an organic light emitting diode (OLED) display, or the like. Processor 310 can send raw display data to touch and display controller 316, and touch and display controller 316 can send signals to touch screen 320. Data can include voltage levels for a plurality of display pixels in touch screen 320 to project an image. In some examples, processor 310 can be configured to process the raw data and send the signals to touch screen 320 directly. Touch and display controller 316 can also detect and track touches or near touches (and any movement or release of the touch) on touch screen 320. For example, touch processor 318 can process data representative of touch or near touches on touch screen 320 (e.g., location and magnitude) and identify touch or proximity gestures (e.g., tap, double tap, swipe, pinch, reverse-pinch, etc.). Processor 310 can convert the detected touch input/gestures into interaction with graphical objects, such as one or more user-interface objects, displayed on touch screen 320 or perform other functions (e.g., to initiate a wake of the device or power on one or more components).

In some examples, touch and display controller 316 can be configured to send raw touch data to processor 310, and processor 310 can process the raw touch data. In some examples, touch and display controller 316 can be process raw touch data itself (e.g., in touch processor 318). The processed touch data (touch input) can be transferred from touch processor 318 to processor 310 to perform the function corresponding to the touch input. In some examples, a separate touch sensor panel and display screen can be used, rather than a touch screen, with corresponding touch controller and display controller.

In some examples, the touch sensing of touch screen 320 can be provided by capacitive touch sensing circuitry (e.g., based on mutual capacitance and/or self-capacitance). For example, touch screen 320 can include touch electrodes arranged as a matrix of small, individual plates of conductive material or as drive lines and sense lines, or in another pattern. The electrodes can be formed from a transparent conductive medium such as ITO or ATO, although other partially or fully transparent and non-transparent materials (e.g., copper) can also be used. In some examples, the electrodes can be formed from other materials including conductive polymers, metal mesh, graphene, nanowires (e.g., silver nanowires) or nanotubes (e.g., carbon nanotubes). The electrodes can be configurable for mutual capacitance or self-capacitance sensing or a combination of mutual and self-capacitance sensing. For example, in one mode of operation electrodes can be configured to sense mutual capacitance between electrodes and in a different mode of operation electrodes can be configured to sense self-capacitance of electrodes. During self-capacitance operation, a touch electrode can be stimulated with an AC waveform, and the self-capacitance to ground of the touch electrode can be measured. As an object approaches the touch electrode, the self-capacitance to ground of the touch electrode can change (e.g., increase). This change in the self-capacitance of the touch electrode can be detected and measured by the touch sensing system to determine the positions of one or more objects when they touch, or come in proximity to without touching, the touch screen. During mutual capacitance operation, a first touch electrode can be stimulated with an AC waveform, and the mutual capacitance between the first touch electrode and a second touch electrode can be measured. As an object approaches the overlapping or adjacent region of the first and second touch electrodes, the mutual capacitance therebetween can change (e.g., decrease). This change in the mutual capacitance can be detected and measured by the touch sensing system to determine the positions of one or more objects when they touch, or come in proximity to without touching, the touch screen. In some examples, some of the electrodes can be configured to sense mutual capacitance therebetween and some of the electrodes can be configured to sense self-capacitance thereof.

Note that one or more of the functions described herein, including measuring and processing physiological signals according to examples of the disclosure, can be performed by firmware stored in memory (or in program storage 302)

and executed by physiological sensor controller 312, touch and display controller 316 or processor 310. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

Referring back to FIG. 1B, light emitters 102A-B can generate light and light detectors 104A-B can measure light at multiple wavelengths $\lambda 1$, $\lambda 2$, $\lambda 3$. In some examples, three light sources 106A-C can be co-located (within a threshold distance of one another, e.g., less than 5 mm) in each of light emitters 102A-B. In some examples, each of the light sources can be driven in a time-multiplexed manner. For example, during a measurement period of duration T (from time $t_0$ to $t_6$), a first light source 106A of light emitter 102A can be driven at wavelength $\lambda 1$ and light can be detected at light detectors 104A-B (from $t_0$ to $t_1$), a second light source 106B of light emitter 102A can be driven at wavelength $\lambda 2$ and light can be detected at light detectors 104A-B (from $t_1$ to $t_2$), a third light source 106C of light emitter 102A can be driven at wavelength $\lambda 3$ and light can be detected at light detectors 104A-B (from $t_2$ to $t_3$), a fourth light source 106A of light emitter 102B can be driven at wavelength $\lambda 1$ and light can be detected at light detectors 104A-B (from $t_3$ to $t_4$), a fifth light source 106B of light emitter 102B can be driven at wavelength $\lambda 2$ and light can be detected at light detectors 104A-B (from $t_4$ to $t_5$), and a sixth light source 106C of light emitter 102B can be driven at wavelength $\lambda 3$ and light can be detected at light detectors 104A-B (from $t_5$ to $t_6$). Ideally, the measurement period can be less than a threshold duration. Reducing the duration of measurement period can allow for the measurements at different wavelengths to be as co-located in time as possible. In some examples, the duration of the measurement period can be less than 100 ms. The above measurements can result in a sample for each channel (e.g., 4 channels of FIG. 1B) at each wavelength (e.g., $\kappa 1$, $\lambda 2$, $\lambda 3$) for the measurement period.

Figure 4:
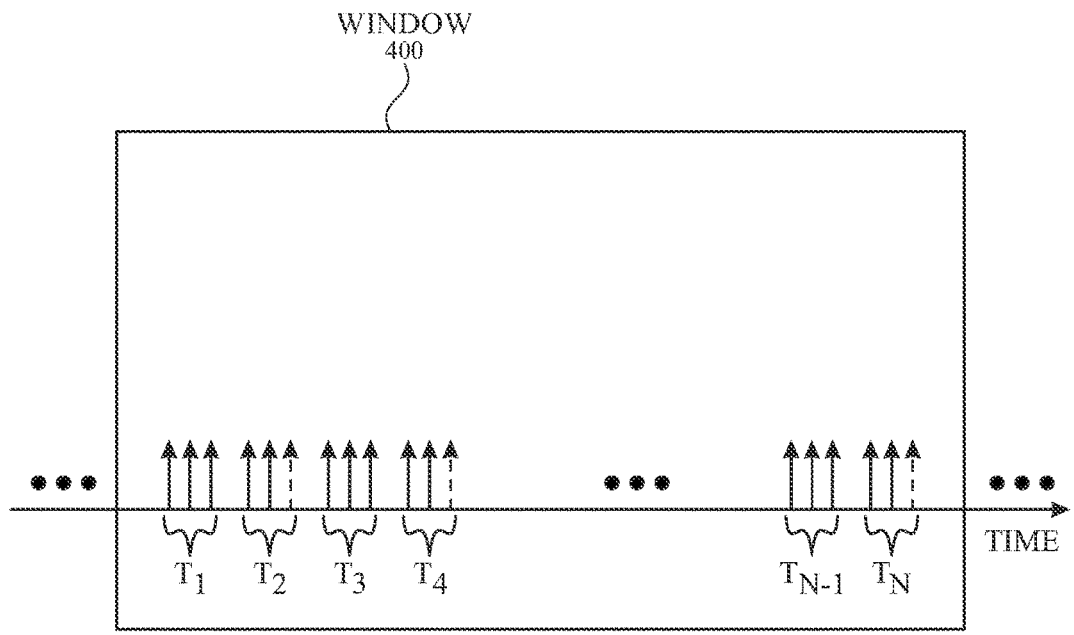
FIG. 4 illustrates a graphical representation of exemplary physiological signal samples according to examples of the disclosure.

FIG. 4 illustrates a graphical representation of physiological signal samples according to examples of the disclosure. FIG. 4 illustrates a window 400 of time including N measurement periods ($T_1$-$T_N$) of duration T for one channel. In some examples, each measurement period can include one sample at wavelengths $\lambda 1$, $\lambda 2$, $\lambda 3$. In some example, each measurement period can include one sample at wavelengths $\lambda 1$ and $\lambda 2$ (which may be used for relative modulation ratio calculation, such as a perfusion index ratio calculation), whereas fewer than all measurement periods can include a sample at wavelength $\lambda 3$ (which, for example, may be used for estimating the contact condition between the physiological sensors and the user's skin). For example, as illustrated in FIG. 4, a sample at wavelength $\lambda 3$ can be taken every other measurement period. In some examples, the sample at wavelength $\lambda 3$ can be taken every third measurement period or a specified number of times (e.g., once, twice, etc.) in the duration of window 400. Sampling the physiological sensor at wavelength $\lambda 3$ less frequently can reduce the power consumption of the device without changing the sampling rate at wavelengths $\lambda 1$ and $\lambda 2$ (which may be used for a relative modulation ratio calculation, such as a perfusion index ratio calculation, to determine oxygen saturation without the need for wavelength $\lambda 3$).

As discussed above, FIG. 4 illustrates sampling for one channel. In some examples with multiple channels, during each measurement period, samples at wavelengths $\lambda 1$, $\lambda 2$ and $\lambda 3$ can be taken for each channel. In some examples with multiple channels, samples at wavelengths $\lambda 1$ and $\lambda 2$ can be taken each for each channel during each measurement period and measurements at wavelength $\lambda 3$ can be taken fewer than each measurement period (e.g., every other or third measurement period, once per window, etc.). Additionally or alternatively, in some examples with multiple channels, samples at wavelengths $\lambda 1$ and $\lambda 2$ can be taken for each channel during each measurement period and measurements at wavelength $\lambda 3$ can be taken for fewer than all channels. For example, a sample at wavelength $\lambda 3$ can be taken for one of the four channels during each measurement period for the four channels. In some examples, a sample at wavelength $\lambda 3$ can be taken for a different one of the four channels during each measurement period for the four channels.

Although illustrated in FIG. 1B as including a light source 106C (e.g., an LED or OLED) configured to generate light at wavelength $\lambda 3$ for each of light emitters 102A-102B (and therefore providing the capability to capture a measurements at wavelength $\lambda 3$ for each channel), in some examples, some light emitters can include a light source 106C configured to generate light at wavelength $\lambda 3$ and some light emitters can not include a light source 106C configured to generate light at wavelength $\lambda 3$. In some examples, the device may include only one light source 106C configured to generate light at wavelength $\lambda 3$ for use in classifying/filtering based on light at wavelength $\lambda 3$. Additionally, or alternatively, although illustrated in FIG. 1B as co-locating light sources 106A-C for each of emitters 102A-102B, in some examples, one or more light sources 106C generating light at wavelength $\lambda 3$ may not be co-located with the one or more light sources 106A-B. Additionally or alternative, in some examples, one or more light sources 106A and 106B may not be co-located.

Although FIG. 4 illustrates a time-multiplexing scheme in which each light source can generate light at different times within the measurement period, in some examples, multi-stimulus techniques can be used to generate light at different wavelengths simultaneously. For example wavelength encoding techniques (or other filtering techniques) can be used to modulate and demodulate light generated at different wavelengths.

Figure 5:
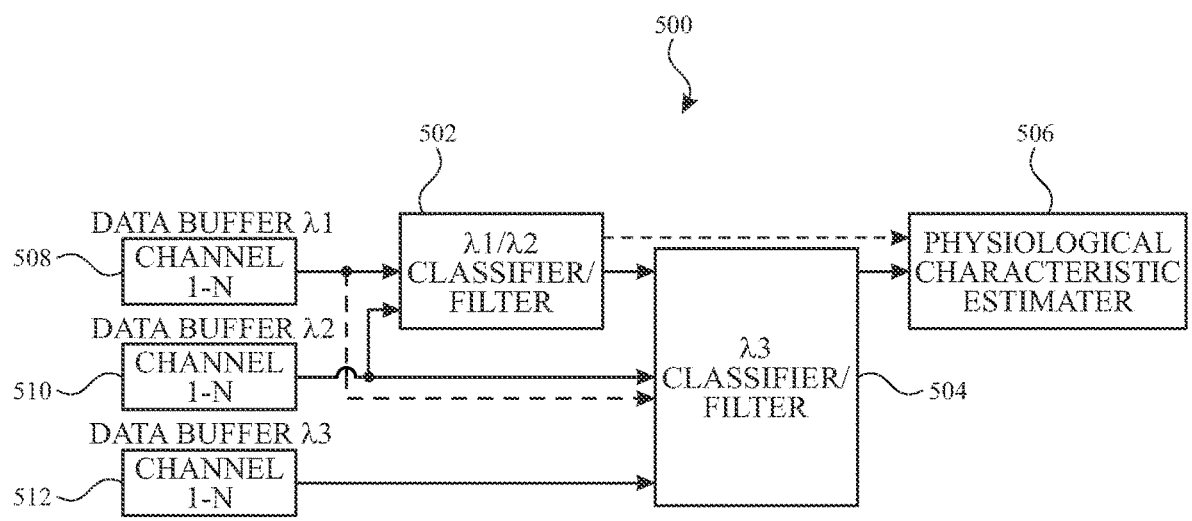
FIG. 5 illustrates exemplary processing circuitry for processing physiological signals according to examples of the disclosure.

FIG. 5 illustrates exemplary processing circuitry for processing physiological signals according to examples of the disclosure. The processing circuitry can be a digital signal processor (DSP) 500 (corresponding to signal processor 314 in FIG. 3). DSP 500 can include a signal classifier/filter 502 for samples at wavelengths $\lambda 1$ and $\lambda 2$, a signal classifier/filter 504 for samples at wavelength $\lambda 3$, and a physiological characteristic estimator 506. Signal classifiers/filters 502, 504 and physiological characteristic estimator 506 can be implemented in hardware, software, firmware or any combination thereof, including one or more signal processing and/or application specific integrated circuits. DSP 500 can also, in some examples, include one or more data buffers or other memory to store data samples from multiple channels and at multiple wavelengths. For example, FIG. 5 illustrates data buffers 508, 510, 512 that can each store measurements for multiple channels at multiple wavelengths, with data buffer 508 storing measurements from multiple channels at wavelength $\lambda 1$, data buffer 510 storing measurements from multiple channels at wavelength $\lambda 2$, and data buffer 512 storing measurements from multiple channels at wavelength $\lambda 3$. In some examples, the size of the data buffers can correspond to the size of window 400 such that the data buffers can store enough data for pulse oximetry. In some examples, the data buffers or other memory storing the data can be accessed by DSP 500 for processing rather than being included as part of DSP 500. It should be understood that other arrangement of data from the multiple channels and wavelengths are possible.

Signal classifier/filter 502 can be used to classify samples at wavelengths $\lambda 1$ and $\lambda 2$. In some examples, the classification can be binary, and samples at wavelengths $\lambda 1$ and $\lambda 2$ for a given channel and measurement period can be classified as "valid" or "invalid." Valid samples can be used for subsequent processing to determine a characteristic of the physiological signal and invalid samples can be rejected from the subsequent processing to determine a characteristic of the physiological signal. In some examples, the classification can provide a confidence measure (e.g., a confidence value) for samples at wavelengths $\lambda 1$ and $\lambda 2$ for a given channel and measurement period. In some examples, the confidence can be assigned as a probability (from 0 to 1) that the sample is valid. In some examples, the confidence can be used to filter samples and/or to weight samples. For example, samples with a confidence below a threshold could be rejected (e.g., <30%) and samples with a confidence above a threshold could be used for subsequent processing (and/or weighted). In some examples, the samples can be weighted in the subsequent processing in accordance with the confidence, where the weighting can be higher for a sample with a higher confidence than the weighting of a sampling with a lower confidence.

In some examples, the classification performed by signal classifier/filter 502 can classify based on signal quality metrics for samples at wavelengths $\lambda 1$ and $\lambda 2$. In some examples, the signal quality metrics can consider correlation between the signals at wavelengths $\lambda 1$ and $\lambda 2$ or a signal-to-noise (SNR) ratio of the signals at each of wavelengths $\lambda 1$ and $\lambda 2$. When the correlation between the signals is above a threshold and/or the SNR of the signals at each of wavelengths $\lambda 1$ and $\lambda 2$ are above a threshold, the sample can be accepted or assigned a higher confidence value. When the correlation between the signals is below a threshold and/or the SNR of the signals at each of wavelengths $\lambda 1$ and $\lambda 2$ are below a threshold, the sample can be rejected or assigned a lower confidence value.

Additionally or alternatively, in some examples, the signal quality metrics can include whether the relative modulation ratio (e.g., PI ratio) is within a range of expected values (e.g., empirically determined) and whether the physiological signal (e.g., PPG signal) has one or more properties of an expected physiological signal (e.g., beat properties such as amplitude, frequency, etc. that can be characteristic of cardiac-induced blood flow). In some examples, the classification can include computing a relative modulation ratio (e.g., PI ratio) for the sample of wavelengths $\lambda 1$ and $\lambda 2$ in a measurement sample for a channel. When the relative modulation ratio for wavelengths $\lambda 1$ and $\lambda 2$ is outside of the range of expected values, for example, the sample can be rejected or can be assigned a lower confidence value, whereas when the relative modulation ratio for wavelengths $\lambda 1$ and $\lambda 2$ is inside of the range of expected values, the sample can be used or can be assigned a higher confidence value. In some examples, the physiological characteristic (e.g., blood saturation) can be estimated from the relative modulation ratio (or be computed directly from the physiological signals without first computing the relative modulation ratio), and the sample can be accepted/rejected or assigned a confidence based on the estimated physiological characteristic. In some examples, multiple samples at wavelengths $\lambda 1$ and $\lambda 2$ in a window (e.g., window 400) can be sampled and the multiple samples in the window can be used/rejected or assigned confidence values based on whether the physiological signals at $\lambda 1$ and $\lambda 2$ represented in the samples in the window meet the one or more morphological characteristics of an expected physiological signal at $\lambda 1$ and $\lambda 2$.

In some examples, signal classifier/filter 502 can output the classification of a sample as "valid" or "invalid." In some examples, signal classifier/filter 502 can output a weighting value or confidence value for the sample. In some examples, the relative modulation ratio (e.g., PI ratio) for $\lambda 1$ and $\lambda 2$ for the sample (or an estimated characteristic for the sample) can be output for use by physiological characteristic estimator 506.

Signal classifier/filter 504 can be used to classify samples at wavelengths $\lambda 1$ and $\lambda 2$ using samples at wavelength $\lambda 3$. In some examples, the classification can be binary, and samples at wavelengths $\lambda 1$ and $\lambda 2$ for a given channel and measurement period can be classified as "valid" or "invalid." Valid samples can be used for subsequent processing to determine a characteristic of the physiological signal and invalid samples can be rejected from the subsequent processing to determine a characteristic of the physiological signal. In some examples, the classification can provide a confidence measure (e.g., a confidence value) for samples at wavelengths $\lambda 1$ and $\lambda 2$ for a given channel and measurement period. In some examples, the confidence can be assigned as a probability (from 0 to 1) that the sample is valid. In some examples, the confidence can be used to filter samples and/or to weight samples. For example, samples with a confidence below a threshold could be rejected (e.g., <30%) and samples with a confidence above a threshold could be used for subsequent processing (and/or weighted). In some examples, the samples can be weighted in the subsequent processing in accordance with the confidence, where the weighting can be higher for a sample with a higher confidence than the weighting of a sampling with a lower confidence.

In some examples, the classification at signal classifier/filter 504 can be performed for each sample at wavelengths $\lambda 1$ and $\lambda 2$. In some examples, the classification at signal classifier/filter 504 can be performed for samples classified as "valid" by signal classifier/filter 502 or classified with a confidence value or weighting above a threshold (e.g., 50%). Although signal classifier/filter 504 is illustrated as following signal classifier/filter 502, it should be understood that this order could be reversed or that the two classifiers/filters can be in parallel rather than in series in the processing flow.

In some examples, the classification performed by signal classifier/filter 504 can be based on signal metrics for samples at wavelength $\lambda 3$. In some examples, the signal metrics can include whether a relative modulation ratio (e.g., perfusion index ratio) based on wavelength $\lambda 3$ meets a threshold. In some examples, the classification can include computing a relative modulation ratio for the sample of wavelengths $\lambda 3$ and $\lambda 2$ or a relative modulation ratio for the sample of wavelengths $\lambda 3$ and $\lambda 1$ in a measurement sample for a channel (e.g., using wavelength $\lambda 1$ or $\lambda 2$ as a reference wavelength). When the relative modulation ratio for wavelengths $\lambda 3$ to $\lambda 1$ or $\lambda 3$ to $\lambda 2$ is outside a threshold relative modulation ratio range, for example, the sample at wavelengths $\lambda 1$ and $\lambda 2$ can be rejected or can be assigned a lower confidence value (or the confidence value from signal classifier/filter 502 can be modified), whereas when the relative modulation ratio for wavelengths $\lambda 3$ to $\lambda 1$ or $\lambda 3$ to $\lambda 2$ is within a threshold relative modulation ratio range, the sample at wavelengths $\lambda 1$ and $\lambda 2$ can be used or can be assigned a higher confidence value (or the confidence value from signal classifier/filter 502 can be modified). Additionally, or alternatively, in some examples, the signal metrics can be based on the relative timing and/or phase between one or more pulses in the measurements at wavelength $\lambda 3$ and measurements at a reference wavelength (e.g., $\lambda 1$ or $\lambda 2$). Additionally or alternatively, in some examples, the signal metrics can be based on the morphology of the signal at wavelength $\lambda 3$ (e.g., waveform characteristics such as amplitude, frequency, etc.) during a window including multiple measurement periods.

In some examples, the threshold relative modulation ratio range for relative modulation ratios using measurements at wavelength $\lambda 3$ can be determined empirically. In some examples, the threshold relative modulation ratio range can vary based on various factors. In some examples, the threshold relative modulation ratio range can have a temperature dependence, and the threshold relative modulation ratio range to use can be selected based on a temperature (e.g., measured by a temperature sensor in device 100). In some examples, the threshold relative modulation ratio range can be dependent on the contact between the physiological sensors and the user's skin (e.g., based on how well strap 146 fastens the physiological sensors to the users skin. In some examples, a calibration measurement can be made when the user begins a physiological signal measurement session (e.g., launches a physiological signal measurement application), when the user puts a wearable device on, or at an initialization stage (e.g., during the initial device setup). It should be understood that temperature dependence and contact dependence are two exemplary factors, but other factors may impact the threshold relative modulation ratio range (e.g., absorption characteristics of the user's tissue), and may be accounted for when selecting the threshold relative modulation ratio range.

In some examples, the relative modulation ratio for wavelengths $\lambda 3$ to $\lambda 1$ or $\lambda 3$ to $\lambda 2$ can be calculated for each sample and each channel. In some examples, one relative modulation ratio for wavelengths $\lambda 3$ to $\lambda 1$ or to $\lambda 2$ can be calculated and used for multiple samples in a window of time (e.g., window 400) and/or for multiple channels. For example, in some examples, each channel can include a light source at wavelength $\lambda 3$ and a measurement at wavelength $\lambda 3$ can be measured for each sample at wavelengths $\lambda 1$ and $\lambda 2$. In some examples, each channel can include a light source at wavelength $\lambda 3$ and a measurement at wavelength $\lambda 3$ can be measured less frequently than for each sample at wavelengths $\lambda 1$ and $\lambda 2$ (e.g., periodically or once per window). In some examples, some channels may not include a light source at wavelength $\lambda 3$ and a measurement at wavelength $\lambda 3$ from a different channel and/or a different sample period can be used.

In some examples, signal classifier/filter 504 can output the classification of a sample at wavelengths $\lambda 1$ and $\lambda 2$ as "valid" or "invalid." In some examples, signal classifier/filter 504 can output a weighting value or confidence value for the sample at wavelengths $\lambda 1$ and $\lambda 2$.

In some examples, classifier/filter 504 can use measurements at additional wavelengths aside from wavelength $\lambda 3$. For example, mathematical or other algorithmic combinations of signals or signal properties from wavelength $\lambda 3$ can be used along with signals or signal properties from wavelength $\lambda 1$, wavelength $\lambda 2$, or other wavelength(s). The mathematical operations can include correlation, division, averaging, etc. The algorithms can include thresholding or machine learning algorithms to classify a measurement sample as "valid" or "invalid", or to weight the sample. In some examples, a time shift between the measurements at wavelength $\lambda 3$ and the measurements at either wavelength $\lambda 1$ or wavelength $\lambda 2$ can be used to classify the sample.

Physiological characteristic estimator 506 can estimate or predict a characteristic from the physiological signal. For example, the information or characteristic can be an oxygen saturation level, such as $SpO_2$. In some examples, the information or characteristic can be estimated based on samples at wavelengths $\lambda 1$ and $\lambda 2$ (or the previously computed relative modulation ratio using wavelengths $\lambda 1$ and $\lambda 2$) classified as "valid" by signal classifiers/filters 502 and 504. The samples at wavelength $\lambda 3$ may be used by signal classifier/filter 504, but not for estimation of the characteristic. In some examples, samples meeting some confidence value threshold can be used and those failing to meet the confidence value threshold can be rejected. In some examples, the samples can all be weighted and used (though some may be weighted to zero and thereby effectively be rejected).

In some examples, a device may include one channel and the oxygen saturation level can be determined instantaneously for each "valid" sample or relative modulation measurement. In some examples, multiple "valid" instantaneous samples/relative modulation ratio measurements within a window of time can be averaged to estimate an oxygen saturation level for the window of time. In some examples, a weighted average can be used for the instantaneous samples/relative modulation ratio measurements with a window of time. The weighting can be applied based on the confidence values (e.g., as a scaling factor). In some examples, the median or mode oxygen saturation level for the window of time can be reported as the estimate for the window of time.

In some examples, a device may include more than one channel. In some examples, an oxygen saturation level can be determined instantaneously for each measurement period based on a mean (weighted or unweighted), a median or a mode of "valid" samples/relative modulation ratio measurement from each channel. In some examples, the oxygen saturation level can be determined for a window of time based on a mean (weighted or unweighted), a median or a mode of "valid" samples/PI measurement from each channel and measurement period in the window. In some examples the oxygen saturation level can be determined for a window of time based on a mean (weighted or unweighted), a median or a mode of the instantaneous oxygen saturation level estimated from multiple channels for a measurement period.

It should be understood that the above processing to estimate the physiological characteristic (e.g., oxygen saturation level) is exemplary, and that other processing is possible to estimate the physiological characteristic.

Figure 6:
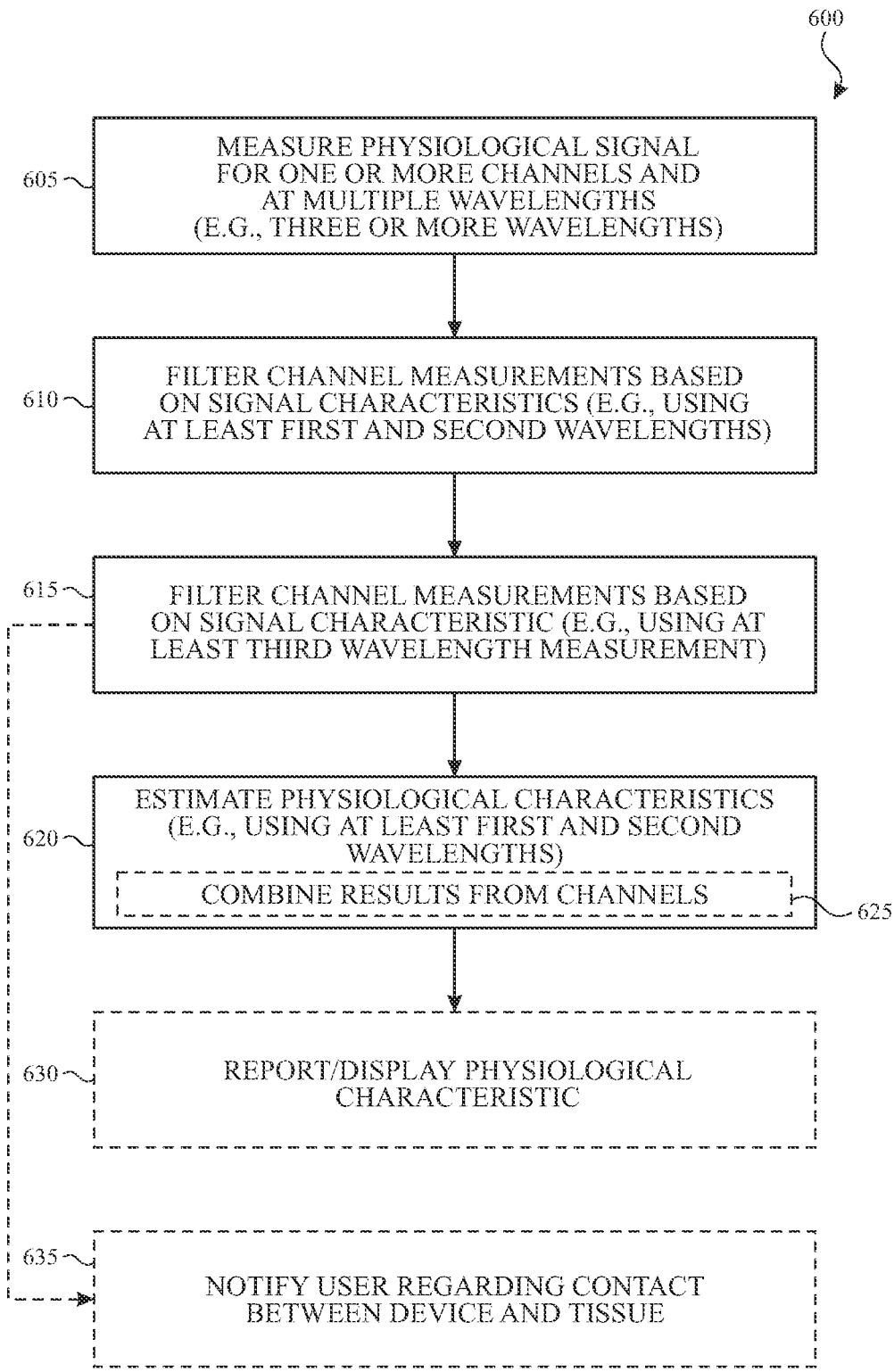
FIG. 6 illustrates an exemplary process for processing physiological signals according to examples of the disclosure.

FIG. 6 illustrates an exemplary process 600 for processing physiological signals according to examples of the disclosure. At 605, physiological signals can be measured (e.g., using light emitters 304, light detectors 306, sensing circuitry 308 and/or controller 312) for one or more channels at multiple wavelengths. Measurements at two (or more) of the wavelengths can be used for estimate the physiological characteristic (e.g., oxygen saturation level). Measurements at a third wavelength can be used for filtering described herein, without being used for estimating the physiological characteristic. In some examples, the physiological signals measured at the multiple wavelengths can be measured using co-located light emitters (e.g., as illustrated in FIGS. 1B and 1D) and can be co-located in time (e.g., within a measurement period for the channel as illustrated in FIG. 4). In some examples, the measurements can be stored in volatile or non-volatile storage (e.g., data buffers 508, 510, 512).

The measurements can be filtered to reject or deemphasize measurements for channels that fail to meet criteria and to process or emphasize measurements for channels that meet the criteria. In some examples, the filtering can be divided into two stages. At 610, the measurements at two (or more) of the wavelengths can be classified or filtered (e.g., by signal classifiers/filters 502) based on characteristics of the measurements at the two (or more) of the wavelengths to reject or deemphasize measurements at the two (or more) of the wavelengths. In some examples, the characteristics of the measurements can examine signal quality metrics of the measurements. In some examples, the signal quality metrics can consider correlation between the signals at wavelengths $\lambda 1$ and $\lambda 2$ and/or a signal-to-noise (SNR) ratio of the signals at each of wavelengths $\lambda 1$ and $\lambda 2$. When the correlation between the signals is above a threshold and/or the SNR of the signals at each of wavelengths $\lambda 1$ and $\lambda 2$ are above a threshold, the sample can be accepted or assigned a higher confidence value. When the correlation between the signals is below a threshold and/or the SNR of the signals at each of wavelengths $\lambda 1$ and $\lambda 2$ are below a threshold, the sample can be rejected or assigned a lower confidence value.

Additionally, or alternatively, in some examples, a relative modulation ratio can be computed from the measurements at a first wavelength and a second wavelength ($\lambda 1$ and $\lambda 2$). When the relative modulation ratio for the first and second wavelengths is outside of a range of values (e.g., predetermined based on empirical measurements), for example, the sample can be rejected or can be assigned a lower confidence value, whereas when the relative modulation ratio for the first and second wavelengths $\lambda 1$ and $\lambda 2$ is inside the range of values, the sample can be used for further processing or can be assigned a higher confidence value. In some examples, the other signal and noise characteristics of the physiological signal (e.g., beat characteristics such as amplitude, frequency, etc. that can be characteristic of blood flow) can be used. In some examples, the relative modulation ratio can be transformed into the units of the physiologic characteristic directly (e.g., from physiological signal measurements of light absorption to an arterial blood oxygen saturation) without first computing the relative modulation ratio as an intermediate value and then transforming the computed relative modulation ratio into a physiological characteristic (e.g., an arterial blood oxygen saturation). In such cases, the sample can be rejected or assigned a lower confidence value when the estimated characteristic is outside a threshold range and can be accepted or assigned a higher confidence value when the estimated characteristic is inside the threshold range.

At 615, the measurements at two (or more) of the wavelengths can be classified or filtered (e.g., by signal classifier/filters 504) based on characteristics of the measurements at the third wavelength ($\lambda 3$) to reject or deemphasize measurements at the two (or more) of the wavelengths. In some examples, the characteristic of the measurements at the third wavelength can predict a condition that may result in inaccurate measurements of the physiological signal characteristic. For example, the condition may be contact condition between the physiological sensor(s) and the user's skin. As described herein, poor contact between a physiological sensor and the user's skin can result in measurements at the first and second wavelengths that may meet signal quality metrics (and thus may not be filtered out by signal classifier/filters 502), but that produce inaccurate estimates of a physiological characteristic. Other conditions may be identified as well, such as unexpected orientation of the physiological sensor relative to the tissue or a transient or permanent tissue anomaly, that may result in inaccurate measurements of the physiological signal characteristic. In some examples, a relative modulation ratio can be computed from measurements at the third wavelength and either the first wavelength or the second wavelength (e.g., $\lambda 3/\lambda 2$ or $\lambda 3/\lambda 1$). In some examples, when the relative modulation ratio using measurements at wavelength $\lambda 3$ is outside a threshold relative modulation ratio range (e.g., less than a first threshold relative modulation ratio and greater than a second threshold relative modulation ratio), for example, the measurements at wavelengths $\lambda 1$ and $\lambda 2$ can be rejected or can be assigned a lower confidence value (or the confidence value at 610 can be modified), whereas when the relative modulation ratio using measurements at wavelength $\lambda 3$ is inside the threshold relative modulation ratio range, the measurements at wavelengths $\lambda 1$ and $\lambda 2$ can be used or can be assigned a higher confidence value (or the confidence value at 610 can be modified). In some examples, the relative modulation ratio can be transformed into the units of the physiologic characteristic directly (e.g., from physiological signal measurements of light absorption to an arterial blood oxygen saturation) without first computing the relative modulation ratio as an intermediate value and then transforming the computed relative modulation ratio into a physiological characteristic (e.g., an arterial blood oxygen saturation).

The use of a relative modulation ratio using wavelength $\lambda 3$ and a reference wavelength is exemplary, and other properties of the measurements at wavelength $\lambda 3$ and a reference wavelength can be used to identify one or more conditions (e.g., contact condition, orientation condition, tissue anomaly condition). Additionally, in some examples, the relative modulation ratio or other properties of the measurements at wavelength $\lambda 3$ and a reference wavelength may respond differently to different conditions, such that different ranges or thresholds may be used to identify each condition. In such cases, the sample can be rejected or assigned a lower confidence value when the estimated characteristic based on wavelength λ3 is outside a threshold range and can be accepted or assigned a higher confidence value when the estimated characteristic based on wavelength λ3 is inside the threshold range.

The filtering at 610 and at 615 can be performed for each sample including measurements at the first and second wavelength for each channel. At 620, a physiological characteristic can be estimated based on the samples. In some examples, the physiological characteristic can be estimated instantaneously (e.g., for each measurement period) or can be estimated over a window of time including multiple measurement periods. In some examples, the instantaneous estimate can include aggregating measurements from multiple channels (at 625). For example, an instantaneous estimate of oxygen saturation level can be computed based on a mean, median or mode of the relative modulation ratios (e.g., perfusion index ratios) at wavelengths λ1 and λ2 for each channel in the measurement period. In some examples, the rejected/filtered samples can be excluded from the estimate. In some examples, the samples can be weighted based on the filtering and thus samples corresponding to poor signal quality metrics or poor contact (or other conditions, such as unexpected orientation of the physiological sensor relative to the tissue or a transient or permanent tissue anomaly, that may result in inaccurate measurements of the physiological signal characteristic) can be deemphasized. In some examples, an estimate of oxygen saturation level over a window can be computed as a mean, median or mode of the instantaneous estimates within the window (or based on a mean, median or mode of the relative modulation ratios (e.g., perfusion index ratios) at wavelengths λ1 and λ2 for each channel in each measurement period within the window). The samples can be filtered or weighted in a similar manner for an estimate of oxygen saturation level over a window as for an instantaneous estimate of oxygen saturation level.

In some examples, the estimated physiological characteristic can be reported to the user at 630. For example, the estimated physiological characteristic can be displayed on the display, stored on the device or transmitted to another device, or be reported with other feedback mechanisms (e.g., audio feedback, haptic feedback, etc.). In some examples, when the physiological characteristic estimates cannot be made with confidence (e.g., due to filtering/classifying rejecting and/or assigning low confidence to estimates of the physiological characteristic), the physiological characteristic may not be displayed (or a notification can be displayed indicating that an estimate cannot be made with confidence).

In some examples, the filtering of channel measurements can be used to notify a user regarding contact between the device and the user's skin at 635. For example, as described herein, the characteristic of the measurements at the third wavelength can predict a contact condition between the physiological sensor(s) and the user's skin (e.g., "good contact" or "bad contact"). Thus, in some examples, this information can notify the user to improve the contact (e.g., by tightening (or loosening) strap 146).

It should be understood that the order of processing illustrated in process 600 can be changed without departing from the scope of the disclosure. For example, filtering at 610 and 615 can be done in series (in the illustrated or reverse order), in parallel, or otherwise combined. Additionally, in some examples, the estimate of the physiologic characteristic for one or more channels at 620 can be done prior to the filtering at 610 or as part of the filtering at 610, and the filtering at 610 can reject or assign a low confidence to characteristic estimates outside of a threshold range and accept or assign a higher confidence to characteristic estimates inside of the threshold range. Additionally, in some examples, the estimate of the physiological characteristic at 620 and the report/display of the physiological characteristic can be skipped when the poor contact condition is determined (e.g., at 615). Additionally, it should be understood that the filtering at 610 and 615, the estimation of the physiological characteristic at 620, and/or the reporting or notifications at 630 and 635 can be performed by processing circuitry in the device (e.g., DSP 500, host processor 310, etc.) or in one or more processing circuits in a different device or distributed between multiple devices.

Although primarily described herein as a reflectance-based system (e.g., for a watch), in some examples, a transmission-based system can be used for robust pulse oximetry. For example, a wearable sensor on a user's earlobe can use transmission-based pulse oximetry using at least wavelengths λ1 and λ2 for estimating the physiological characteristic and wavelength λ3 for filtering/classifying. In some examples, a wearable sensor on a user's finger can use a combination of transmission-based pulse oximetry techniques using at least wavelengths λ1 and λ2 for estimating the physiological characteristic and using reflectance-based techniques to acquire physiological signals at wavelength λ3 for filtering/classifying.

As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, a user's heart rate may allow a user to track or otherwise gain insights about their health or fitness levels.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data Therefore, according to the above, some examples of the disclosure are directed to a method. The method can comprise: measuring physiological signals including a first physiological signal at a first wavelength, a second physiological signal at a second wavelength and a third physiological signal at a third wavelength; determining whether one or more criteria are met for the physiological signals, the one or more criteria including a criterion based on the third physiological signal at the third wavelength; in accordance with the determination that the one or more criteria are met for the physiological signals, estimating a physiological characteristic using the first physiological signal at the first wavelength and the second physiological signal at the second wavelength, without using the third physiological signal at the third wavelength; and in accordance with the determination that the one or more criteria are not met for the physiological signals, forgo estimating the physiological characteristic using the first physiological signal at the first wavelength and the second physiological signal at the second wavelength. Additionally or alternatively to one or more of the examples disclosed above, in some examples, the criterion based on the third physiological signal at the third wavelength requires that a relative modulation ratio of the third physiological signal at the third wavelength to the first physiological signal at the first wavelength or to the second physiological signal at the second wavelength is within a threshold range. Additionally or alternatively to one or more of the examples disclosed above, in some examples, in some examples, the criterion based on the third physiological signal at the third wavelength can be based on a comparison of the morphology of the third physiological signal at the third wavelength with the morphology of the first physiological signal at the first wavelength or the morphology of the second physiological signal at the second wavelength. Additionally or alternatively to one or more of the examples disclosed above, in some examples, in some examples, the criterion based on the third physiological signal at the third wavelength can be based on a comparison of the timing of the third physiological signal at the third wavelength with the timing of the first physiological signal at the first wavelength or the timing of the second physiological signal at the second wavelength. Additionally or alternatively to one or more of the examples disclosed above, in some examples, estimating the physiological characteristic using the first physiological signal at the first wavelength and the second physiological signal at the second wavelength can comprise determining a relative modulation ratio of the first physiological signal at the first wavelength to the second physiological signal at the second wavelength. Additionally or alternatively to one or more of the examples disclosed above, in some examples, the first wavelength can be within a first wavelength range from 620 nm-750 nm, the second wavelength can be within a second wavelength range from 700 nm-1100 nm, and the third wavelength can be within a third wavelength range from 400 nm-570 nm. Additionally or alternatively to one or more of the examples disclosed above, in some examples, the first physiological signal at the first wavelength, the second physiological signal at the second wavelength and the third physiological signal at the third wavelength can be measured simultaneously or within a threshold time period. Additionally or alternatively to one or more of the examples disclosed above, in some examples, the first physiological signal at the first wavelength and the second physiological signal at the second wavelength can be measured simultaneously or within a first threshold time period, and the third physiological signal at the third wavelength can be measured outside the first threshold time period, but within a second threshold time period from the measurement of the first physiological signal at the first wavelength and the second physiological signal at the second wavelength. Additionally or alternatively to one or more of the examples disclosed above, in some examples, the first physiological signal at the first wavelength, the second physiological signal at the second wavelength and the third physiological signal at the third wavelength can be measured by a first light detector based on reflected or scattered light from light sources including a first light source configured to generate light at the first wavelength, a second light source configured to generate light at the second wavelength and a third light source configured to generate light at the third wavelength. The first light source, the second light source and the third light source can be located within a threshold distance from one another. Additionally or alternatively to one or more of the examples disclosed above, in some examples, the one or more criteria can include a criterion that requires that a relative modulation ratio of the first physiological signal at the first wavelength to the second physiological signal at the second wavelength is within a threshold range of values. Additionally or alternatively to one or more of the examples disclosed above, in some examples, the one or more criteria can include a criterion that requires that the physiological characteristic predicted by the first physiological signal at the first wavelength and the second physiological signal at the second wavelength is within a threshold range of values. Some examples of the disclosure are directed to a non-transitory computer-readable medium. The non-transitory computer readable storage medium can store instructions, which when executed by one or more processors, can cause the one or more processors to perform any of the above methods.

Some examples of the disclosure are directed to an electronic device. The electronic device can comprise one or more light emitters configured to illuminate tissue with light at a first wavelength, a second wavelength and a third wavelength; a light detector configured to detect reflections or scattering of the light at the first wavelength, the second wavelength and the third wavelength; and a processor. The processor can be configured to: measure, from the light detector, physiological signals including a first physiological signal at the first wavelength, a second physiological signal at the second wavelength and a third physiological signal at the third wavelength; determine whether one or more criteria are met for the physiological signals, the one or more criteria including a criterion based on the third physiological signal at the third wavelength; in accordance with the determination that the one or more criteria are met for the physiological signals, estimate a physiological characteristic using the first physiological signal at the first wavelength and the second physiological signal at the second wavelength, without using the third physiological signal at the third wavelength; and in accordance with the determination that the one or more criteria are not met for the physiological signals, forgo estimating the physiological characteristic using the first physiological signal at the first wavelength and the second physiological signal at the second wavelength. Additionally or alternatively to one or more of the examples disclosed above, in some examples, the one or more light emitters can be configured to illuminate tissue with light at the first wavelength and the second wavelength at a first sampling rate, and configured to illuminate tissue with light at the third wavelength at a second sampling rate different than the first sampling rate. Additionally or alternatively to one or more of the examples disclosed above, in some examples, the one or more light emitters can be configured to illuminate tissue with light at the first wavelength at a first sampling rate, light at the second wavelength at a second sampling rate, and light at the third wavelength at a third sampling rate. The first, second and third sampling rates can be different. Additionally or alternatively to one or more of the examples disclosed above, in some examples, the one or more light emitters can be configured to illuminate tissue with light at the first wavelength, the second wavelength and the third wavelength at an equal sampling rate. Additionally or alternatively to one or more of the examples disclosed above, in some examples, the one or more light emitters can be configured to illuminate tissue at the first wavelength, at the second wavelength and at the third wavelength simultaneously or within a threshold time period. Additionally or alternatively to one or more of the examples disclosed above, in some examples, the one or more light emitters can be configured to illuminate tissue at the first wavelength and at the second wavelength simultaneously or within a first threshold time period, and the one or more light emitters can be configured to illuminate tissue at the third wavelength outside the first threshold time period, but within a second threshold time period from illuminating tissue at the first wavelength and at the second wavelength. Additionally or alternatively to one or more of the examples disclosed above, in some examples, the one or more emitters can comprise a first light source configured to generate light at the first wavelength, a second light source configured to generate light at the second wavelength and a third light source configured to generate light at the third wavelength. The first light source, the second light source and the third light source are located within a threshold distance. Additionally or alternatively to one or more of the examples disclosed above, in some examples, the one or more emitters can comprise a first light source configured to generate light at the first wavelength, a second light source configured to generate light at the second wavelength and a third light source configured to generate light at the third wavelength. The first light source and the second light source can be located within a threshold distance, and the third light source can be outside the threshold distance. Additionally or alternatively to one or more of the examples disclosed above, in some examples, the criterion based on the third physiological signal at the third wavelength requires that a relative modulation ratio of the third physiological signal at the third wavelength to the first physiological signal at the first wavelength or to the second physiological signal at the second wavelength is within a threshold range. Additionally or alternatively to one or more of the examples disclosed above, in some examples, in some examples, the criterion based on the third physiological signal at the third wavelength can be based on a comparison of the morphology of the third physiological signal at the third wavelength with the morphology of the first physiological signal at the first wavelength or the morphology of the second physiological signal at the second wavelength. Additionally or alternatively to one or more of the examples disclosed above, in some examples, in some examples, the criterion based on the third physiological signal at the third wavelength can be based on a comparison of the timing of the third physiological signal at the third wavelength with the timing of the first physiological signal at the first wavelength or the timing of the second physiological signal at the second wavelength. Additionally or alternatively to one or more of the examples disclosed above, in some examples, estimating the physiological characteristic using the first physiological signal at the first wavelength and the second physiological signal at the second wavelength can comprise determining a relative modulation ratio of the first physiological signal at the first wavelength to the second physiological signal at the second wavelength. Additionally or alternatively to one or more of the examples disclosed above, in some examples, the first wavelength can be within a first wavelength range from 620 nm-750 nm, the second wavelength can be within a second wavelength range from 700 nm-1100 nm, and the third wavelength can be within a third wavelength range from 400 nm-570 nm. Additionally or alternatively to one or more of the examples disclosed above, in some examples, the one or more criteria can include a criterion that requires that a relative modulation ratio of the first physiological signal at the first wavelength to the second physiological signal at the second wavelength is within a threshold range of values. Additionally or alternatively to one or more of the examples disclosed above, in some examples, the one or more criteria can include a criterion that requires that the physiological characteristic predicted by the first physiological signal at the first wavelength and the second physiological signal at the second wavelength is within a threshold range of values.

Some examples of the disclosure are directed to a method. The method can comprise: measuring physiological signals including a first physiological signal at a first wavelength, a second physiological signal at a second wavelength and a third physiological signal at a third wavelength; determining whether one or more criteria are met for the physiological signals, the one or more criteria including a criterion based on the third physiological signal at the third wavelength; assigning a confidence value to the first physiological signal and the second physiological, and estimating a physiological characteristic using the first physiological signal, the second physiological signal, and the assigned confidence value. In accordance with the determination that the one or more criteria are met for the physiological signals, assigning a first confidence value to the first physiological signal and the second physiological signal, and in accordance with the determination that the one or more criteria are not met for the physiological signals, assigning a second confidence value, less than the first confidence value, to the first physiological signal and the second physiological signal. Some examples of the disclosure are directed to a non-transitory computer-readable medium. The non-transitory computer readable storage medium can store instructions, which when executed by one or more processors, can cause the one or more processors to perform any of the above methods. Some examples of the disclosure are directed to an electronic device. The electronic device can comprise one or more light emitters configured to generate light at (e.g. to illuminate tissue with) light at a first wavelength, a second wavelength and a third wavelength; a light detector configured to detect reflections or scattering of the light at the first wavelength, the second wavelength and the third wavelength; and a processor. The processor can be configured to perform any of the above methods.

Some examples of the disclosure are directed to a method. The method can comprise: measuring physiological signals including a plurality of samples, each of the plurality of samples including a first physiological signal at a first wavelength, a second physiological signal at a second wavelength, and a third physiological signals at a third wavelength; determining, for each of the plurality of samples, whether one or more criteria are met for the first physiological signal, second physiological signal, and third physiological signal of the sample, the one or more criteria including a criterion based on the third physiological signal of the sample; and estimating a physiological characteristic. The estimation of the physiological characteristic can use the first physiological signal and the second physiological signal of one or more samples determined to meet the one or more criteria, without using the first physiological signal and the second physiological signal of one or more samples determined to not meet the one or more criteria. Some examples of the disclosure are directed to a non-transitory computer-readable medium. The non-transitory computer readable storage medium can store instructions, which when executed by one or more processors, can cause the one or more processors to perform any of the above methods. Some examples of the disclosure are directed to an electronic device. The electronic device can comprise one or more light emitters configured to generate light at (e.g. to illuminate tissue with) light at a first wavelength, a second wavelength and a third wavelength; a light detector configured to detect reflections or scattering of the light at the first wavelength, the second wavelength and the third wavelength; and a processor. The processor can be configured to perform any of the above methods.

Some examples of the disclosure are directed to a method. The method can comprise: measuring physiological signals including a plurality of samples, each sample including a first physiological signal at a first wavelength and a second physiological signal at a second wavelength; measuring one or more third physiological signals at a third wavelength; determining, for each of the plurality of samples, whether one or more criteria are met for the first physiological signal of the sample, the second physiological signal of the sample, and at least one of the one or more third physiological signals, the one or more criteria including a criterion based on the at least one of the one or more third physiological signals; and estimating a physiological characteristic. The estimation of the physiological characteristic can use the first physiological signal and the second physiological signal of one or more samples determined to meet the one or more criteria, without using the first physiological signal and the second physiological signal of one or more samples determined to not meet the one or more criteria. Some examples of the disclosure are directed to a non-transitory computer-readable medium. The non-transitory computer readable storage medium can store instructions, which when executed by one or more processors, can cause the one or more processors to perform any of the above methods. Some examples of the disclosure are directed to an electronic device. The electronic device can comprise one or more light emitters configured to generate light at (e.g. to illuminate tissue with) light at a first wavelength, a second wavelength and a third wavelength; a light detector configured to detect reflections or scattering of the light at the first wavelength, the second wavelength and the third wavelength; and a processor. The processor can be configured to perform any of the above methods.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. A method comprising:
    measuring physiological signals including a first physiological signal at a first wavelength, a second physiological signal at a second wavelength and a third physiological signal at a third wavelength;
    determining whether one or more criteria are met for the physiological signals, the one or more criteria including a criterion based on the third physiological signal at the third wavelength; and
    in accordance with the determination that the one or more criteria are met for the physiological signals, estimating a physiological characteristic using the first physiological signal at the first wavelength and the second physiological signal at the second wavelength, without using the third physiological signal at the third wavelength.

2. The method of claim 1, further comprising:
    assigning a confidence value to the first physiological signal and the second physiological signal, including:
        in accordance with the determination that the one or more criteria are met for the physiological signals, assigning a first confidence value to the first physiological signal and the second physiological signal; and
        in accordance with the determination that the one or more criteria are not met for the physiological signals, assigning a second confidence value, less than the first confidence value, to the first physiological signal and the second physiological signal;
    wherein the physiological characteristic is further estimated using the assigned confidence value.

3. The method of claim 1, wherein the criterion based on the third physiological signal at the third wavelength requires that a relative modulation ratio of the third physiological signal at the third wavelength to the first physiological signal at the first wavelength or to the second physiological signal at the second wavelength is within a threshold range.

4. The method of claim 1, wherein estimating the physiological characteristic using the first physiological signal at the first wavelength and the second physiological signal at the second wavelength comprises determining a relative modulation ratio of the first physiological signal at the first wavelength to the second physiological signal at the second wavelength.

5. The method of claim 1, wherein the first physiological signal at the first wavelength, the second physiological signal at the second wavelength and the third physiological signal at the third wavelength are measured simultaneously or within a threshold time period.

6. The method of claim 1, wherein the first physiological signal at the first wavelength and the second physiological signal at the second wavelength are measured simultaneously or within a first threshold time period, and the third physiological signal at the third wavelength is measured outside the first threshold time period, but within a second threshold time period from the measurement of the first physiological signal at the first wavelength and the second physiological signal at the second wavelength.

7. The method of claim 1, wherein the first physiological signal at the first wavelength, the second physiological signal at the second wavelength and the third physiological signal at the third wavelength are measured by a first light detector based on reflected or scattered light from light sources including a first light source configured to generate light at the first wavelength, a second light source configured to generate light at the second wavelength and a third light source configured to generate light at the third wavelength, wherein the first light source, the second light source and the third light source are located within a threshold distance from one another.

8. The method of claim 1, wherein the one or more criteria include a criterion that requires that a relative modulation ratio of the first physiological signal at the first wavelength to the second physiological signal at the second wavelength is within a threshold range of values.

9. The method of claim 1, wherein the one or more criteria include a criterion that requires that the physiological characteristic predicted by the first physiological signal at the first wavelength and the second physiological signal at the second wavelength is within a threshold range of values.

10. An electronic device comprising:
one or more light emitters configured to illuminate tissue with light at a first wavelength, a second wavelength and a third wavelength;
a light detector configured to detect reflections or scattering of the light at the first wavelength, the second wavelength and the third wavelength; and
a processor configured to:
measure, from the light detector, physiological signals including a first physiological signal at the first wavelength, a second physiological signal at the second wavelength and a third physiological signal at the third wavelength;
determine whether one or more criteria are met for the physiological signals, the one or more criteria including a criterion based on the third physiological signal at the third wavelength; and
in accordance with the determination that the one or more criteria are met for the physiological signals, estimate a physiological characteristic using the first physiological signal at the first wavelength and the second physiological signal at the second wavelength, without using the third physiological signal at the third wavelength.

11. The electronic device of claim 10, the processor further configured to:
assign a confidence value to the first physiological signal and the second physiological signal, including:
in accordance with the determination that the one or more criteria are met for the physiological signals, assign a first confidence value to the first physiological signal and the second physiological signal; and
in accordance with the determination that the one or more criteria are not met for the physiological signals, assign a second confidence value, less than the first confidence value, to the first physiological signal and the second physiological signal;
wherein the physiological characteristic is further estimated using the assigned confidence value.

12. The electronic device of claim 10, wherein the one or more light emitters is configured to illuminate tissue with light at the first wavelength and the second wavelength at a first sampling rate, and configured to illuminate tissue with light at the third wavelength at a second sampling rate different than the first sampling rate.

13. The electronic device of claim 10, wherein the one or more light emitters is configured to illuminate tissue with light at the first wavelength, the second wavelength and the third wavelength at an equal sampling rate.

14. The electronic device of claim 10, wherein the one or more light emitters is configured to illuminate tissue at the first wavelength, at the second wavelength and at the third wavelength simultaneously or within a threshold time period.

15. The electronic device of claim 10, wherein the one or more light emitters is configured to illuminate tissue at the first wavelength and at the second wavelength simultaneously or within a first threshold time period, and the one or more light emitters is configured to illuminate tissue at the third wavelength outside the first threshold time period, but within a second threshold time period from illuminating tissue at the first wavelength and at the second wavelength.

16. The electronic device of claim 10, wherein the one or more light emitters comprises a first light source configured to generate light at the first wavelength, a second light source configured to generate light at the second wavelength and a third light source configured to generate light at the third wavelength, wherein the first light source, the second light source and the third light source are located within a threshold distance.

17. The electronic device of claim 10, wherein the one or more light emitters comprises a first light source configured to generate light at the first wavelength, a second light source configured to generate light at the second wavelength and a third light source configured to generate light at the third wavelength, wherein the first light source and the second light source are located within a threshold distance, and wherein the third light source is outside the threshold distance.

18. A non-transitory computer readable storage medium storing instructions, which when executed by one or more processors, cause the one or more processors to perform a method, the method comprising:
measuring physiological signals including a first physiological signal at a first wavelength, a second physiological signal at a second wavelength and a third physiological signal at a third wavelength;
determining whether one or more criteria are met for the physiological signals, the one or more criteria including a criterion based on the third physiological signal at the third wavelength; and
in accordance with the determination that the one or more criteria are met for the physiological signals, estimating a physiological characteristic using the first physiological signal at the first wavelength and the second physiological signal at the second wavelength, without using the third physiological signal at the third wavelength.

19. The non-transitory computer readable storage medium of claim 18, the method further comprising:
assigning a confidence value to the first physiological signal and the second physiological signal, including:
in accordance with the determination that the one or more criteria are met for the physiological signals, assigning a first confidence value to the first physiological signal and the second physiological signal; and
in accordance with the determination that the one or more criteria are not met for the physiological signals, assigning a second confidence value, less than the first confidence value, to the first physiological signal and the second physiological signal;

wherein the physiological characteristic is further estimated using the assigned confidence value.

20. The non-transitory computer readable storage medium of claim 18, wherein the criterion based on the third physiological signal at the third wavelength requires that a relative modulation ratio of the third physiological signal at the third wavelength to the first physiological signal at the first wavelength or to the second physiological signal at the second wavelength is within a threshold range.

\* \* \* \* \*